(12) United States Patent
Kozlowski et al.

(10) Patent No.: US 10,787,441 B2
(45) Date of Patent: Sep. 29, 2020

(54) HEPATITIS C VIRUS INHIBITORS

(71) Applicant: Merck Sharp & Dohme Corp., Rahway, NJ (US)

(72) Inventors: Joseph A. Kozlowski, Princeton, NJ (US); Wensheng Yu, Edison, NJ (US); Bin Hu, Shanghai (CN); Bin Zhong, Shanghai (CN); Jinglai Hao, Shanghai (CN); Dahai Wang, Shanghai (CN); Zhixin Lei, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/094,621

(22) PCT Filed: Apr. 17, 2017

(86) PCT No.: PCT/US2017/027850
§ 371 (c)(1),
(2) Date: Oct. 18, 2018

(87) PCT Pub. No.: WO2017/184476
PCT Pub. Date: Oct. 26, 2017

(65) Prior Publication Data
US 2019/0127355 A1 May 2, 2019

(30) Foreign Application Priority Data
Apr. 21, 2016 (WO) ................ PCT/CN2016/079871

(51) Int. Cl.
| | | |
|---|---|---|
| *A61K 31/4178* | (2006.01) | |
| *C07D 405/14* | (2006.01) | |
| *A61K 38/21* | (2006.01) | |
| *A61K 38/19* | (2006.01) | |
| *A61K 45/06* | (2006.01) | |

(52) U.S. Cl.
CPC ........ *C07D 405/14* (2013.01); *A61K 31/4178* (2013.01); *A61K 38/19* (2013.01); *A61K 38/21* (2013.01); *A61K 45/06* (2013.01)

(58) Field of Classification Search
CPC .......................... A61K 31/4178; C07D 407/14
USPC ........................................... 514/397; 549/384
See application file for complete search history.

(56) References Cited

U.S. PATENT DOCUMENTS

| | | |
|---|---|---|
| 8,871,759 B2 | 10/2014 | Coburn et al. |
| 9,090,661 B2 | 7/2015 | Coburn et al. |
| 9,254,292 B2 | 2/2016 | Coburn et al. |
| 9,555,038 B2 | 1/2017 | Yu et al. |
| 2014/0121238 A1 | 5/2014 | Davioud-Charvet et al. |
| 2014/0199264 A1 | 7/2014 | Coburn et al. |
| 2014/0213571 A1 | 7/2014 | Liverton et al. |

FOREIGN PATENT DOCUMENTS

| | | |
|---|---|---|
| WO | 2010111534 A1 | 9/2010 |
| WO | 2012003642 A1 | 1/2012 |
| WO | 2012050848 A1 | 4/2012 |
| WO | WO2012050918 A2 | 4/2012 |
| WO | 2012068234 A2 | 5/2012 |
| WO | 2015089810 A1 | 6/2015 |
| WO | 2015094998 A1 | 6/2015 |
| WO | 2018035005 | 2/2018 |
| WO | 2018035006 | 2/2018 |

OTHER PUBLICATIONS

Adrian M. Dibisceglie, et al, "The Ultimate Challenges of Hepatitis C", Scientific American, Inc., 1999, pp. 80-85.
D.L Thomas, et al, "The Hepatitis C Virus", Curr. Top Microbiol. Immunol., 2000, pp. 25-41, US.
G. Kuo, et al, "An Assay for Circulating Antibodies to a Major Etiologic Virus of Human Non-A, Non-B Hepatitis", Science, 1980, pp. 362-364, vol. 244, US.
Hadziyannis et al., Peginterfern-alpha2a-and Ribavirin Combination therapy in Chronic Hepatitis C: A randomized Study of Treatment Duration and Ribavirin Dose, Ann. Intern. Med., 2004, 346-355, 140.
International Search Report and Written Opinion for PCT/US2017/027850, dated Jul. 21, 2017, 9 pages.
Michael P. Manns, et al, "Peginterferon Alfa-2B Plus Ribavirin Compared With Interferon Alfa-2B Plus Ribavirin for Initial Treatment of Chronic Hepatitis C: A Randomised Trial", The Lancet, 2001, pp. 958-965, vol. 358, US.

(Continued)

*Primary Examiner* — Jeffrey H Murray
(74) *Attorney, Agent, or Firm* — Jeffrey P. Bergman; Catherine D. Fitch

(57) ABSTRACT

A compound of Formula (I) or (II), for treating or preventing an HCV infection in a subject.

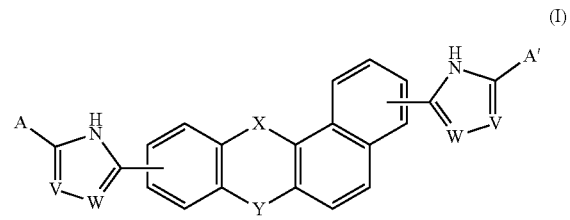

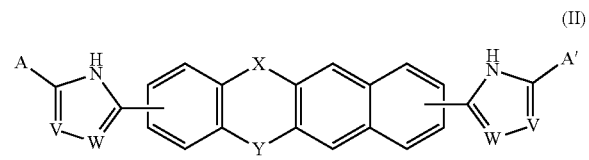

13 Claims, No Drawings

(56) References Cited

OTHER PUBLICATIONS

Michael W. Fried, et al, "Peginterferon Alfa-2a Plus Ribavirin for Chronic Hepatitis C Virus Infection", N. Engl. J. Med., 2002, pp. 975-982, vol. 347, No. 13, US.
Nobuyuki Kato, "Molecular Virology of Hepatitis C Virus", Acta Med. Okayama, 2001, pp. 133-159, vol. 55, No. 3, US.
Nobuyuki Kato, et al, "Moleclar Cloning of the Human Hepatitis C Virus Genome From Japanese Patients With Non-A, Non-B Hepatitis", Proc. Natl. Acad. Sci., 1990, pp. 9524-9528, vol. 87, US.
Thierry Poynard, et al, "Randomised Trial of Interferon Alpha2B Plus Ribavirin for 48 Weeks or for 24 Weeks Versus Interferon Alpha2B Plus Placebo for 48 Weeks for Treatment of Chronic Infection With Hepatitis C Virus", The Lancet, 1998, pp. 1426-1432, vol. 352, US.

HEPATITIS C VIRUS INHIBITORS

CROSS-REFERENCE TO RELATED APPLICATIONS

This application is the national stage application under 35 U.S.C. 371 of International Patent Application No. PCT/US17/027850, filed Apr. 17, 2017, which claims priority to International Patent Application No. PCT/CN2016/079871, filed Apr. 21, 2016. Each of the aforementioned applications is incorporated by reference in its entirety.

FIELD OF THE INVENTION

Provided herein are hepatitis C virus inhibitor compounds, pharmaceutical compositions comprising the compounds, and preparation thereof. Also provided are methods of their use for treating an HCV infection.

BACKGROUND OF THE INVENTION

Hepatitis C virus (HCV) is known to cause at least 80% of post transfusion hepatitis and a substantial proportion of sporadic acute hepatitis (Kuo et al., *Science* 1989, 244, 362-364; Thomas, *Curr. Top. Microbiol. Immunol.* 2000, 25-41). Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (Di Besceglie et al., *Scientific American* 1999, October, 80-85; Boyer et al., *J. Hepatol.* 2000, 32, 98-112).

HCV is an enveloped virus containing a positive-sense single-stranded RNA genome of approximately 9.4 kb (Kato et al., *Proc. Natl. Acad. Sci. USA* 1990, 87, 9524-9528; Kato, *Acta Medica Okayama* 2001, 55, 133-159). The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as an internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

Presently, the most effective HCV therapy employs a combination of alpha-interferon and ribavirin, leading to sustained efficacy in about 40% of patients (Poynard et al., *Lancet* 1998, 352, 1426-1432). Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load (Manns et al., *Lancet* 2001, 358, 958-965; Fried et al., *N. Engl. J. Med.* 2002, 347, 975-982; Hadziyannis et al., *Ann. Intern. Med.* 2004, 140, 346-355). Thus, there is a clear and unmet need to develop effective therapeutics for the treatment of HCV infections.

SUMMARY OF THE INVENTION

A compound of Formulas (I) or (II),

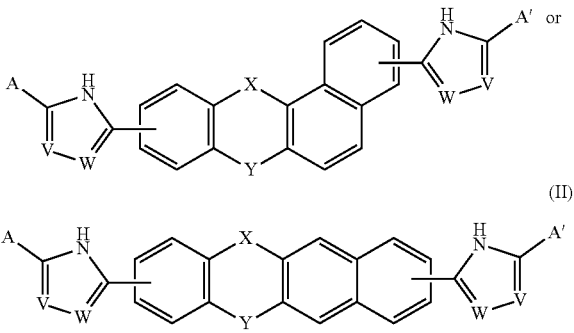

or a pharmaceutically acceptable salt thereof, where
X is —O—, —C(O)—, —C($R^A R^B$)—, $NR^A$, or $SO_2$;
Y is —O—, —C(O)—, —C($R^A R^B$)—, $NR^A$, or $SO_2$;
V is C or N;
W is C or N;
$R^A$ is H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, 6 to 10-membered bicyclic heterocycloalkyl, $C_6$-$C_{10}$ aryl, or —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said 6 to 10-membered bicyclic heterocycloalkyl, or said $C_6$-$C_{10}$ aryl group, can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);
$R^B$ is H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, 6 to 10-membered bicyclic heterocycloalkyl, $C_6$-$C_{10}$ aryl, or —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said 6 to 10-membered bicyclic heterocycloalkyl, or said $C_6$-$C_{10}$ aryl group, can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);
A is:

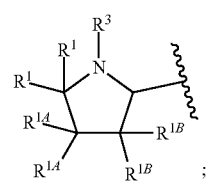

A' is:

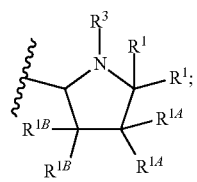

each occurrence of $R^1$ is independently selected from H, $C_1$-$C_6$ alkyl, $C_1$-$C_6$ haloalkyl, $C_3$-$C_7$ cycloalkyl, and halo;
each occurrence of $R^{1A}$ is independently selected from H, $C_1$-$C_6$ alkyl, $C_1$-$C_6$ haloalkyl, $C_3$-$C_7$ cycloalkyl, and halo, or one $R^{1A}$ group and an $R^1$ group that are attached to same ring, together with the ring carbon atoms to which they are attached, can combine to form a fused $C_3$-$C_7$ cycloalkyl group, or two $R^{1A}$ groups that are attached to the same carbon atom, and the common carbon atom to which they are attached, can combine to form a spirocyclic $C_3$-$C_7$ cycloalkyl group;
each occurrence of $R^{1B}$ is independently H, $C_1$-$C_6$ alkyl, $C_1$-$C_6$ haloalkyl, $C_3$-$C_7$ cycloalkyl, or halo, or an $R^{1B}$ group and an $R^{1A}$ group that are attached to the same ring, together with the carbon atoms to which they are attached, can combine to form a fused $C_3$-$C_7$ cycloalkyl group, or an $R^{1B}$ group and an $R^1$ group that are attached to the same ring, can combine to form a bridging group having the formula —$CH_2$— or —$CH_2CH_2$—;
each occurrence of $R^3$ is independently H, —C(O)—C($R^4$)$_2$NHC(O)O—$R^5$, —C(O)O—$R^5$, C(O)NH$R^5$ or —C(O)—C($R^4$)$_2$N$R^7R^8$.
each occurrence of $R^4$ is independently selected from H, $C_1$-$C_6$ alkyl, $C_1$-$C_6$ haloalkyl, $C_6$-$C_{10}$ aryl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group, said $C_6$-$C_{10}$ aryl group and said $C_3$-$C_7$ cycloalkyl group can be optionally substituted with up to 5 groups, each independently selected from halo, —CN, $C_1$-$C_6$ alkyl, $C_1$-$C_6$ haloalkyl, $C_3$-$C_7$ cycloalkyl, —O—$C_1$-$C_6$ alkyl, —N($R^6$)$_2$ and —O—($C_1$-$C_6$ haloalkyl), and wherein said $C_3$-$C_7$ cycloalkyl group can be optionally fused to a 4 to 6-membered monocyclic heterocycloalkyl group, and wherein said 4 to 8-membered monocyclic heterocycloalkyl group and said $C_3$-$C_7$ cycloalkyl group can be substituted on a ring carbon atom with a spirocyclic $C_3$-$C_6$ cycloalkyl group; and wherein said $C_3$-$C_7$ cycloalkyl group can be substituted on a ring carbon atom with a spirocyclic 3 to 6-membered monocyclic heterocycloalkyl group, and wherein two $R^4$ groups, that are attached to a common carbon atom, together with the common carbon atom to which they are attached, can join to form a $C_3$-$C_7$ cycloalkyl group;
each occurrence of $R^5$ is independently selected from $C_1$-$C_6$ alkyl, $C_3$-$C_7$ cycloalkyl and $C_6$-$C_{10}$ aryl;
each occurrence of $R^6$ is independently selected from H, $C_1$-$C_6$ alkyl and $C_3$-$C_7$ cycloalkyl;
each occurrence of $R^7$ is independently H, $C_1$-$C_6$ alkyl, $C_1$-$C_6$ haloalkyl, $C_3$-$C_7$ cycloalkyl, or phenyl, or $R^7$ and $R^8$, together with the nitrogen atom to which they are attached, form a 3 to 6-membered monocyclic heterocycloalkyl group; and
each occurrence of $R^8$ is independently H, $C_1$-$C_6$ alkyl, $C_1$-$C_6$ haloalkyl, $C_3$-$C_7$ cycloalkyl, or phenyl, or $R^7$ and $R^8$, together with the nitrogen atom to which they are attached, form a 3 to 6-membered monocyclic heterocycloalkyl group,
provided that at least one of V and W is N.

Further provided herein are pharmaceutical compositions comprising a compound of Formulas I or II, including a single enantiomer, a racemic mixture, a diastereomer, a mixture of diastereomers, or an isotopic variant thereof, or a pharmaceutically acceptable salt or solvate thereof, and optionally one or more pharmaceutically acceptable excipients or carriers.

Provided herein is a method for treating or preventing an HCV infection in a subject, which comprises administering to the subject a compound of Formulas I or II, including a single enantiomer, a racemic mixture, a diastereomer, a mixture of diastereomers, or an isotopic variant thereof, or a pharmaceutically acceptable salt or solvate thereof.

Provided herein is a method for treating, preventing, or ameliorating one or more symptoms of a liver disease or disorder associated with an HCV infection in a subject, comprising administering to the subject a compound of Formulas I or II, including a single enantiomer, a racemic mixture, a diastereomer, a mixture of diastereomers, or an isotopic variant thereof, or a pharmaceutically acceptable salt or solvate thereof.

Provided herein is a method for inhibiting replication of a virus in a host, comprising contacting the host with a compound of Formulas I or II, including a single enantiomer, a racemic mixture, a diastereomer, a mixture of diastereomers, or an isotopic variant thereof, or a pharmaceutically acceptable salt or solvate thereof.

DETAILED DESCRIPTION

In one embodiment of the invention, the compound of Formula (I) is

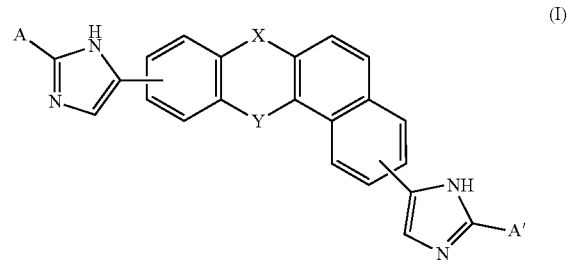

(I)

and the compound of Formula (II) is

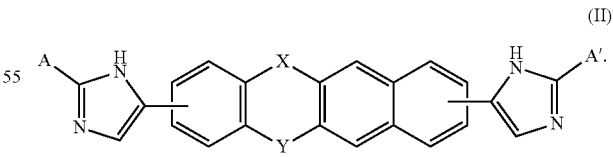

(II)

In one embodiment of the invention, $R^1$ is H
In one embodiment of the invention, $R^A$ and $R^B$ are independently H, halo, or —$C_1$-$C_6$ alkyl.
In another embodiment of the invention, $R^A$ and $R^B$ are independently H, fluoro, —$CH_3$ or —$CH_2CH_3$.
In another embodiment of the invention, $R^{1A}$ is H or fluoro
In another embodiment of the invention, $R^{1B}$ is H In another embodiment of the invention, each $R^3$ is independently H, —C(O)CH(CH(CH$_3$)$_2$)(NHC(O)OCH$_3$), —C(O)OC(CH$_3$)$_3$, C(O)NHC(CH$_3$)$_3$,

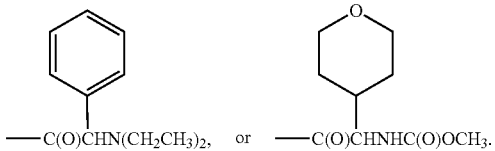

In another embodiment of the invention, each $R^4$ is independently H, —CH(CH$_3$)$_3$,

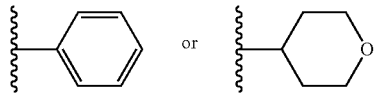

In another embodiment of the invention, each $R^5$ is independently CH$_3$ or C(CH$_3$)$_3$.

In another embodiment of the invention, $R^7$ and $R^8$ are independently —C$_1$-C$_6$ alkyl.

In another embodiment of the invention, $R^7$ and $R^8$ are independently H or —CH$_2$CH$_3$.

In another embodiment of the invention, A and A' are each independently

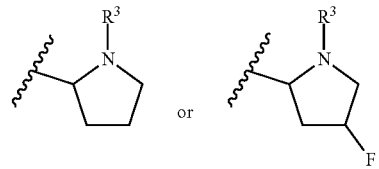

In another embodiment of the invention, the compound is one of the following:

| Compound | IUPAC Name |
|---|---|
| 1 | methyl [(1R)-1-({(2R)-2-[5-(9-{2-[(2R)-1-{(2S)-2-[(methoxycarbonyl)amino]-3-methylbutanoyl}pyrrolidin-2-yl]-1H-imidazol-5-yl}-7-oxo-7H-benzo[c]xanthen-3-yl)-1H-imidazol-2-yl]pyrrolidin-1-yl}carbonyl)-2-methylpropyl]carbamate |
| 2 | methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-12-methyl-12H-benzo[a]xanthen-9-yl)-1H-imidazol-2-yl]pyrrolidin-1-yl}carbonyl)-2-methylpropyl]carbamate |
| 3 | methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-12-methyl-12H-benzo[a]xanthen-9-yl)-1H-imidazol-2-yl]pyrrolidin-1-yl}carbonyl)-2-methylpropyl]carbamate |
| 4 | methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-7-methyl-7H-benzo[c]xanthen-9-yl)-1H-imidazol-2-yl]pyrrolidin-1-yl}carbonyl)-2-methylpropyl]carbamate |
| 5 | methyl [(1S)-1-({(2S)-2-[5-(12-ethyl-3-{2-[(2S)-1-{(2S)-2-[(methoxycarbonyl)amino]-3-methylbutanoyl}pyrrolidin-2-yl]-1H-imidazol-5-yl}-12H-benzo[a]xanthen-9-yl)-1H-imidazol-2-yl]pyrrolidin-1-yl}carbonyl)-2-methylpropyl]carbamate |
| 6 | methyl [(1S)-1-({(2S)-2-[5-(12-ethyl-3-{2-[(2S)-1-{(2S)-2-[(methoxycarbonyl)amino]-3-methylbutanoyl}pyrrolidin-2-yl]-1H-imidazol-5-yl}-12H-benzo[a]xanthen-9-yl)-1H-imidazol-2-yl]pyrrolidin-1-yl}carbonyl)-2-methylpropyl]carbamate |
| 7 | methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-12,12-dimethyl-12H-benzo[a]xanthen-9-yl)-1H-imidazol-2-yl]pyrrolidin-1-yl}carbonyl)-2-methylpropyl]carbamate |
| 8 | methyl [(1R)-1-({(2S)-2-[5-(12,12-diethyl-3-{2-[(2S)-1-{(2S)-2-[(methoxycarbonyl)amino]-3-methylbutanoyl}pyrrolidin-2-yl]-1H-imidazol-5-yl}-12H-benzo[a]xanthen-9-yl)-1H-imidazol-2-yl]pyrrolidin-1-yl}carbonyl)-2-methylpropyl]carbamate |
| 9 | methyl [(1R)-1-({(2S)-2-[5-(12,12-diethyl-9-{2-[(2S)-1-{(2S)-2-[(methoxycarbonyl)amino]-3-methylbutanoyl}pyrrolidin-2-yl]-1H-imidazol-5-yl}-12H-benzo[b]xanthen-3-yl)-1H-imidazol-2-yl]pyrrolidin-1-yl}carbonyl)-2-methylpropyl]carbamate |
| 10 | blank |
| 11 | dimethyl [(12-methyl-12H-benzo[a]xanthene-3,9-diyl)bis{1H-imidazole-5,2-diyl(2S)pyrrolidine-2,1-diyl[(1S)-2-oxo-1-(tetrahydro-2H-pyran-4-yl)ethane-2,1-diyl]}]biscarbamate |
| 12 | dimethyl [(12-methyl-12H-benzo[a]xanthene-3,9-diyl)bis{1H-imidazole-5,2-diyl(2S)pyrrolidine-2,1-diyl[(1S)-2-oxo-1-(tetrahydro-2H-pyran-4-yl)ethane-2,1-diyl]}]biscarbamate |
| 13 | dimethyl [(12,12-dimethyl-12H-benzo[a]xanthene-3,9-diyl)bis{1H-imidazole-5,2-diyl(2S)pyrrolidine-2,1-diyl[(1S)-2-oxo-1-(tetrahydro-2H-pyran-4-yl)ethane-2,1-diyl]}]biscarbamate |
| 14 | dimethyl [(12-ethyl-12H-benzo[a]xanthene-3,9-diyl)bis{1H-imidazole-5,2-diyl(2S)pyrrolidine-2,1-diyl[(1S)-2-oxo-1-(tetrahydro-2H-pyran-4-yl)ethane-2,1-diyl]}]biscarbamate |

-continued

| Compound | IUPAC Name |
|---|---|
| 15 | dimethyl [(12-ethyl-12H-benzo[a]xanthene-3,9-diyl)bis{1H-imidazole-5,2-diyl(2S)pyrrolidine-2,1-diyl[(1S)-2-oxo-1-(tetrahydro-2H-pyran-4-yl)ethane-2,1-diyl]}]biscarbamate |
| 16 | methyl [(1R)-2-[(2R)-2-{5-[12,12-diethyl-9-(2-{(2R)-1-[(2S)-2-[(methoxycarbonyl)amino]-2-(tetrahydro-2H-pyran-4-yl)acetyl]pyrrolidin-2-yl}-1H-imidazol-5-yl)-12H-benzo[a]xanthen-3-yl]-1H-imidazol-2-yl}pyrrolidin-1-yl]-2-oxo-1-(tetrahydro-2H-pyran-4-yl)ethyl]carbamate |
| 17 | methyl [(1R)-2-[(2S)-2-{5-[12,12-diethyl-9-(2-{(2S)-1-[(2S)-2-[(methoxycarbonyl)amino]-2-(tetrahydro-2H-pyran-4-yl)acetyl]pyrrolidin-2-yl}-1H-imidazol-5-yl)-12H-benzo[b]xanthen-3-yl]-1H-imidazol-2-yl}pyrrolidin-1-yl]-2-oxo-1-(tetrahydro-2H-pyran-4-yl)ethyl]carbamate |
| 18 | 3-{2-[(2S,4R)-4-fluoropyrrolidin-2-yl]-1H-imidazol-5-yl}-9-{2-[(2S,4S)-4-fluoropyrrolidin-2-yl]-1H-imidazol-5-yl}-12H-benzo[a]xanthen-12-one |
| 19 | 6-fluoro-2,9-bis{2-[(2S,4S)-4-fluoropyrrolidin-2-yl]-1H-imidazol-5-yl}-12H-benzo[b]xanthen-12-one |
| 20 | di-tert-butyl (2S,2'S)-2,2'-[(12-oxo-12H-benzo[a]xanthene-3,9-diyl)bis(1H-imidazole-5,2-diyl)]dipyrrolidine-1-carboxylate |
| 21 | (2S,4R,2'S,4'S)-2,2'-[(12-oxo-12H-benzo[a]xanthene-3,9-diyl)bis(1H-imidazole-5,2-diyl)]bis(N-tert-butyl-4-fluoropyrrolidine-1-carboxamide) |
| 22 | di-tert-butyl (2S,4R,2'S,4'S)-2,2'-[(12-oxo-12H-benzo[a]xanthene-3,9-diyl)bis(1H-imidazole-5,2-diyl)]bis(4-fluoropyrrolidine-1-carboxylate) |
| 23 | (2S,4S,2'S,4'S)-2,2'-[(6-fluoro-12-oxo-12H-benzo[b]xanthene-2,9-diyl)bis(1H-imidazole-5,2-diyl)]bis(N-tert-butyl-4-fluoropyrrolidine-1-carboxamide) |
| 24 | di-tert-butyl (2S,4S,2'S,4'S)-2,2'-[(6-fluoro-12-oxo-12H-benzo[b]xanthene-2,9-diyl)bis(1H-imidazole-5,2-diyl)]bis(4-fluoropyrrolidine-1-carboxylate) |
| 25 | methyl [(1S)-1-({(2S)-2-[5-(10-{2-[(2S)-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate |
| 26 | methyl [(1S)-1-({(2S)-2-[5-(6-fluoro-9-{2-[(2S)-1-{(2S)-2-[(methoxycarbonyl)amino]-3-methylbutanoyl}pyrrolidin-2-yl]-1H-imidazol-5-yl}-12-oxo-12H-benzo[b]xanthen-2-yl)-1H-imidazol-2-yl]pyrrolidin-1-yl}carbonyl)-2-methylpropyl]carbamate |
| 27 | methyl [(1S)-1-({(2S,4R)-4-fluoro-2-[5-(10-{2-[(2S,4R)-4-fluoro-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate |
| 28 | methyl [(1S)-1-({(2S,4R)-4-fluoro-2-[5-(9-{2-[(2S,4R)-4-fluoro-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate |
| 29 | methyl [(1S)-1-({(2S,4R)-4-fluoro-2-[5-(6-fluoro-9-{2-[(2S,4R)-4-fluoro-1-{(2S)-2-[(methoxycarbonyl)amino]-3-methylbutanoyl}pyrrolidin-2-yl]-1H-imidazol-5-yl}-12-oxo-12H-benzo[b]xanthen-2-yl)-1H-imidazol-2-yl]pyrrolidin-1-yl}carbonyl)-2-methylpropyl]carbamate |
| 30 | dimethyl [(12-oxo-12H-benzo[a]xanthene-3,9-diyl)bis{1H-imidazole-5,2-diyl(2S)pyrrolidine-2,1-diyl[(1S)-2-oxo-1-(tetrahydro-2H-pyran-4-yl)ethane-2,1-diyl]}]biscarbamate |
| 31 | 3,9-bis(2-{(2S,4R)-1-[(2R)-2-(diethylamino)-2-phenylacetyl]-4-fluoropyrrolidin-2-yl}-1H-imidazol-5-yl)-12H-benzo[a]xanthen-12-one |
| 32 | dimethyl [(12-oxo-12H-benzo[a]xanthene-3,9-diyl)bis{1H-imidazole-5,2-diyl[(2S,4R)-4-fluoropyrrolidine-2,1-diyl][(1S)-2-oxo-1-(tetrahydro-2H-pyran-4-yl)ethane-2,1-diyl]}]biscarbamate |
| 33 | methyl [(1S)-1-({(2S)-2-[5-(9-{2-[(2S)-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate |

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The term "host" refers to a unicellular or multicellular organism in which a virus can replicate, including, but not limited to, a cell, cell line, and animal, such as a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers to an amount, concentration, or dosage of a compound that is required for 50% inhibition of a maximal response in an assay that measures such a response.

The term "$CC_{50}$" refers to an amount, concentration, or dosage of a compound that results in 50% reduction of the viability of a host. In certain embodiments, the $CC_{50}$ of a compound is the amount, concentration, or dosage of the compound that is required to reduce the viability of cells treated with the compound by 50%, in comparison with cells untreated with the compound.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "hepatitis C virus" or "HCV" refers to a viral species or a variant thereof, a pathogenic strain of which causes hepatitis C. Examples of HCV include, but are not limited to, HCV genotypes 1, 2, 3, 4, 5, 6, 7, 8, 9, 10, 11, and subtype 1a, 1b, 1c, 2a, 2b, 2c, 3a, 3b, 4a, 4b, 4c, 4d, 4e, 5a, 6a, 7a, 7b, 8a, 8b, 9a, 10a, and 11a. In certain embodiments, an HCV variant is an HCV species that contains a protein substantially homologous to a native HCV protein, i.e., a protein having one or more naturally or non-naturally occurring amino acid deletions, insertions or substitutions (e.g., derivatives, homologs, and fragments), as compared to the amino acid sequence of the native protein. The amino acid sequence of a protein of an HCV variant is at least about 80% identical, at least about 90% identical, or at least about 95% identical to a native HCV protein. In certain embodiments, the HCV variant contains an NS5A protein variant.

The term "NS5A" refers to nonstructural protein 5A of an HCV, or a variant thereof. NS5A variants include proteins substantially homologous to a native NS5A, i.e., proteins having one or more naturally or non-naturally occurring amino acid deletions, insertions or substitutions (e.g., NS5A derivatives, homologs, and fragments), as compared to the amino acid sequence of a native NS5A. The amino acid sequence of an NS5A variant is at least about 80% identical, at least about 90% identical, or at least about 95% identical to a native NS5A.

The term "alkyl" refers to a linear or branched saturated monovalent hydrocarbon radical, wherein the alkyl may optionally be substituted with one or more substituents Q as described herein. For example, $C_{1-4}$ alkyl refers to a linear saturated monovalent hydrocarbon radical of 1 to 4 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-4}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "halo" refers to fluoro, chloro, bromo, or iodo groups.

The term "haloalkyl" refers to alkyl radicals substituted with one or more, e.g., 1, 2, 3, or 4, etc., halo groups.

The term "cycloalkyl" refers to a non-aromatic mono- or multicyclic ring system comprising about 3 to about 7 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

The term "heterocycloalkyl" refers to a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include azetidinyl, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. The heterocycloalkyl rings of this invention can be "bridged heterocycloalkyl rings. The term "bridged heterocycloalkyl"" (or "bridged heterocyclyl") means a heterocycloalkyl group as defined above having an alkylene chain (generally a 1 or 2 carbon alkylene chain, not counting the atoms in the ring to which the alkylene chain is bound) bridging two carbon atoms in the ring.

The term "aryl" refers to an aromatic monocyclic or multicyclic ring system comprising about 6 to about 14 carbon atoms, preferably about 6 to about 10 carbon atoms. Non-limiting examples of suitable aryl groups include phenyl and naphthyl.

The term "alkylene" refers a chain comprising at least one —($CH_2$)— group. Examples of alkylene chains include, but are not limited to: —$(CH_2)_{1-6}$—, —$(CH_2)_{1-4}$—, —$(CH_2)_{1-2}$— and —$(CH_2)$—.

The term "optionally substituted" is intended to mean that a group or substituent, such as an alkyl, may be substituted with one or more, in one embodiment, one, two, three, or four, substituents Q, each of which is independently selected from, e.g., (a) oxo (=O), cyano (—CN), halo, or nitro (—$NO_2$); (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents $Q^a$; and (c) —C(O)$R^a$, —C(O)O$R^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OP(O)(OR$^e$)$_2$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)(OR$^a$R$^d$, —$CH_2$P(O)(OR$^a$)R$^d$, —$CH_2$OP(O)(OR$^e$)$_2$, —$CH_2$OC(O)C(R$^a$)$_2$NR$^b$R$^c$, —SR$^a$, —S(O)R$^a$, —S(O)$_2$R$^a$, —S(O)NR$^b$R$^3$, or —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$; and each R$^e$ is independently (i) hydrogen; (ii) a monovalent cation, in one embodiment, Na$^+$ or K$^+$; (iii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iv) two R$^e$ together are a divalent cation, in one embodiment, Mg$^{2+}$ or Ca$^{2+}$. As used herein, all groups that can be substituted are "optionally substituted," unless otherwise specified.

In one embodiment, each $Q^a$ is independently selected from of (a) oxo, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OP(O)(OR$^n$)$_2$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$NR$^g$R$^h$, —P(O)(OR$^f$)R$^k$, —$CH_2$P(O)(OR$^f$)R$^k$, —SR$^f$, —S(O)R$^f$, —S(O)$_2$R$^f$, —S(O)NR$^g$R$^h$, or —S(O)$_2$NR$^g$R$^h$; wherein each R$^f$, R$^g$, R$^h$, and R$^k$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^g$ and R$^h$ together with the N atom to which they are attached form heterocyclyl; and each R$^h$ is independently (i) hydrogen; (ii) a monovalent cation, in one embodiment, Na$^+$ or K$^+$; (iii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iv) two R$^n$ together are a divalent cation, in one embodiment, Mg$^{2+}$ or Ca$^{2+}$.

The terms "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I) iodine-125 ($^{125}$I) iodine-127 ($^{127}$I) iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^{3}$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I) iodine-125 ($^{125}$I), iodine-129 ($^{129}$I) and iodine-131 ($^{131}$I). It will be understood that, in a compound as provided herein, any hydrogen can be $^{2}$H, for example, or any carbon can be $^{13}$C, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a single enantiomer, a racemic mixture, a diastereomer, a mixture of diastereomers, or an isotopic variant thereof; or a pharmaceutically acceptable salt or solvate thereof" has the same meaning as the phrase "a single enantiomer, a racemic mixture, a diastereomer, a mixture of diastereomers, or an isotopic variant of the compound referenced therein; or a pharmaceutically acceptable salt or solvate of the compound referenced therein, or a single enantiomer, a racemic mixture, a diastereomer, a mixture of diastereomers, or an isotopic variant of the compound referenced therein."

HCV has a single positive-stranded RNA genome having about 9.6 kb in length that encodes a large polyprotein having about 3010 amino acids. This precursor polyprotein is then processed into a range of structural proteins, including core protein, C, and envelope glycoproteins, E1 and E2; and non-structural proteins, including NS2, NS3, NS4A, NS4B, NS5A, and NS5B, by host signal peptidases and two viral proteases, NS2-3 and NS3. The nonstructural protein 5A (NS5A) is a multifunctional protein essential for HCV replication. Because of its vital role in viral replication, HCV NS5A protein has been actively pursued as a drug target for developing anti-HCV therapy.

Provided herein are pharmaceutical compositions comprising a compound provided herein, e.g., a compound of Formulas I or II, as an active ingredient, including a single enantiomer, a racemic mixture, a diastereomer, a mixture of diastereomers, or an isotopic variant thereof; or a pharmaceutically acceptable salt or solvate thereof; in combination with a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or disaccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The compound provided herein may be administered alone, or in combination with one or more other compounds provided herein. The pharmaceutical compositions that comprise a compound a compound of Formulas I or II, including a single enantiomer, a racemic mixture, a diastereomer, a mixture of diastereomers, or an isotopic variant thereof; or a pharmaceutically acceptable salt or solvate thereof, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration. The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration. The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

The pharmaceutical compositions provided herein can be formulated as a modified release dosage form. As used herein, the term "modified release" refers to a dosage form in which the rate or place of release of the active ingredient (s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Provided herein are methods for treating or preventing a hepatitis C viral infection in a subject, which comprises administering to the subject a therapeutically effective amount of a compound of Formulas I or II, including a single enantiomer, a racemic mixture, a diastereomer, a mixture of diastereomers, or an isotopic variant thereof; or a pharmaceutically acceptable salt or solvate thereof.

In another embodiment, provided herein are methods for treating, preventing, or ameliorating one or more symptoms of a liver disease or disorder associated with an HCV infection, comprising administering to a subject a therapeutically effective amount of a compound of Formulas I or II, including a single enantiomer, a racemic mixture, a diastereomer, a mixture of diastereomers, or an isotopic variant thereof; or a pharmaceutically acceptable salt or solvate thereof. Non-limiting examples of diseases associated with HCV infection include chronic hepatitis, cirrhosis, hepatocarcinoma, or extra hepatic manifestation.

In yet another embodiment, provided herein are methods for treating or preventing a drug-resistant hepatitis C viral infection in a subject, which comprises administering to the subject a therapeutically effective amount of a compound a compound of Formulas I or II, including a single enantiomer, a racemic mixture, a diastereomer, a mixture of diastereomers, or an isotopic variant thereof or a pharmaceutically acceptable salt or solvate thereof.

In yet another embodiment, provided herein are methods for treating, preventing, or ameliorating one or more symptoms of a liver disease or disorder associated with a drug-resistant HCV infection, comprising administering to a subject a therapeutically effective amount of a compound of Formulas I or II, including a single enantiomer, a racemic mixture, a diastereomer, a mixture of diastereomers, or an isotopic variant thereof or a pharmaceutically acceptable salt or solvate thereof. Non-limiting examples of diseases associated with drug-resistant HCV infection include chronic hepatitis, cirrhosis, hepatocarcinoma, or extra hepatic manifestation.

In certain embodiments, the HCV infection is caused by a hepatitis C virus or variant thereof as described herein.

In certain embodiments, the drug-resistant HCV is resistant to an anti-HCV agent. In certain embodiments, the anti-HCV agent is an interferon. In certain embodiments, the anti-HCV agent is ribaririn. In certain embodiments, the anti-HCV agent is amantadine. In certain embodiments, the anti-HCV agent is an interleukin. In certain embodiments, the anti-HCV agent is a phenanthrenequinone. In certain embodiments, the anti-HCV agent is a thiazolidine. In certain embodiments, the anti-HCV agent is a benzanilide. In certain embodiments, the anti-HCV agent is a helicase inhibitor. In certain embodiments, the anti-HCV agent is a nucleotide analogue. In certain embodiments, the anti-HCV agent is a gliotoxin. In certain embodiments, the anti-HCV agent is a cerulenin. In certain embodiments, the anti-HCV agent is an antisense phopshorothioate ologodexoynucleotide. In certain embodiments, the anti-HCV agent is an inhibitor of IRES-dependent translation. In certain embodiments, the anti-HCV agent is a ribozyme. In certain embodiments, the anti-HCV agent is a cyclophilin inhibitor. In certain embodiments, the anti-HCV agent is SYC-635.

In certain embodiments, the anti-HCV agent is a protease inhibitor. In certain embodiments, the anti-HCV agent is a cysteine protease inhibitor. In certain embodiments, the anti-HCV agent is a caspase inhibitor. In certain embodiments, the anti-HCV agent is GS 9450. In certain embodiments, the anti-HCV agent is a serine protease inhibitor. In certain embodiments, the anti-HCV agent is an NS3/4A serine protease inhibitor. In certain embodiments, the anti-HCV agent is a serine protease inhibitor selected from ABT-450, faldaprevir (BI-201335), asunaprevir (BMS-650032), boceprevir (SCH 503034), danoprevir (ITMN-191/R7227), GS-9256, GS-9451, IDX136, IDX316, IDX320, MK-5172, SCH900518, telaprevir (VX-950), TMC 435, vaniprevir (MK-7009), VX-985, and mixtures thereof.

In certain embodiments, the anti-HCV agent is a polymerase inhibitor. In certain embodiments, the anti-HCV agent is an NS5B polymerase inhibitor. In certain embodiments, the anti-HCV agent is a polymerase inhibitor selected from ABT-072, ABT-333, AG-02154, ANA598, ANA773, deleobuvir (BI 207127), GS-9190, GS-9669, HCV-796, IDX184, IDX375, JTK-109, MK-0608, MK-3281, NM283, PF-868554, PSI-879, PSI-938, PSI-6130, PSI-7851, sofosbuvir (PSI-7977), R1626, R7128, RG7128, VCH-759, VCH-916, VX-222 (VCH-222), and mixtures thereof. In certain embodiments, the NS5B polymerase inhibitor is a nucleotide inhibitor. In certain embodiments, the NS5B polymerase inhibitor is a 2'-C-methylnucleoside. In certain embodiments, the NS5B polymerase inhibitor is a 2'-F-2'-C-methylnucleoside. In certain embodiments, the NS5B polymerase inhibitor is a non-nucleoside inhibitor. In certain embodiments, the NS5B polymerase inhibitor is a benzofuran, benzothiadiazine, or thiophene.

In certain embodiments, the anti-HCV agent is an NS5A inhibitor. In certain embodiments, the anti-HCV agent is an NS5A inhibitor selected from daclatasvir (BMS-790052), BMS-824393, ledipasvir (GS-5885), GSK2336805, PPI-668, and mixtures thereof.

In certain embodiments, the drug-resistance of the HCV infection is caused by an HCV variant. In certain embodiments, the HCV variant contains an NS3 protein variant. In certain embodiments, the NS3 protein variant contains a mutation or deletion. In certain embodiments, the NS3 protein variant contains one or more mutations and/or deletions at the amino acid positions of 9, 16, 18, 23, 36, 39, 40, 41, 43, 54, 55, 65, 67, 70, 71, 80, 89, 109, 138, 155, 156, 162, 168, 170, 174, 176, 179, 260, and 489. In certain embodiments, the NS3 protein variant contains one or more mutations and/or deletions at the amino acid positions of 16, 23, 36, 39, 41, 43, 54, 55, 80, 89, 109, 138, 155, 156, 168, 170, 174, 176, 260, and 489. In certain embodiments, the NS3 protein variant contains one or more mutations and/or deletions at the amino acid positions of 36, 54, 155, 156, 168, and 170. In certain embodiments, the NS3 protein variant contains one, two, or more mutations and/or deletions, each independently selected from C16S, V23A, V36A, V36G, V36L, V36M, A39V, Q41R, F43C, F43I, F43S, F43V, T54A, T54S, V55A, Q80K, Q80G, Q80H, Q80L, Q80R, P89R, R109K, S138T, R155G, R155I, R155K, R155L, R155M, R155Q, R155S, R155T, E56G, E56I, E56S, E56T, E56V, D168A, D168E, D168G, D168H, D168I, D168N, D168T, D168V, D168Y, V170A, V170T, S174K, S174N, E176K, T260A, and S489L, provided that there is only one mutation or deletion at a given amino acid position in the NS3 protein variant. In certain embodiments, the NS3 protein variant contains one, two, or more mutations and/or deletions, each independently selected from R155K, E56S, E56T, D168V, and T260A, provided that there is only one mutation or deletion at a given amino acid position in the NS3 protein variant.

In certain embodiments, the HCV variant contains an NS4A protein variant. In certain embodiments, the NS4A protein variant contains a mutation or deletion. In certain embodiments, the NS4A protein variant contains a mutation at the amino acid position of 23. In certain embodiments, the NS4A protein variant contains the V23A mutation.

In certain embodiments, the HCV variant contains an NS4B protein variant. In certain embodiments, the NS4B protein variant contains a mutation or deletion. In certain embodiments, the NS4B protein variant contains a mutation at the amino acid position of 15. In certain embodiments, the NS4B protein variant contains the E15G mutation.

In certain embodiments, the HCV variant contains an NS5A protein variant. In certain embodiments, the NS5A protein variant contains a mutation or deletion. In certain embodiments, the NS5A protein variant contains one or more mutations and/or deletions at the amino acid positions of 23, 28, 30, 31, 32, 37, 54, 58, 63, and 93. In certain embodiments, the NS5A protein variant contains one or more mutations and/or deletions at the amino acid positions of 23, 24, 28, 30, 31, 32, 37, 54, 58, 63, 93, 295, 318, 320, 356, 404, and 442. In certain embodiments, the NS5A protein variant contains one or more mutations and/or deletions at the amino acid positions of 24, 28, 30, 31, 32, 54, 93, 295, and 318. In certain embodiments, the NS5A protein variant contains one, two, or more mutations and/or deletions, each independently selected from L23F, L28M, L28T, M28T, ΔQ30, Q30E, Q30H, Q30K, Q30R, ΔR30, R30E, R30Q, L31F, L31M, L31V, P32L, F37L, H54Y, Q54H, P58H, P58S, I63V, Y93C, Y93H, Y93N, and Y93S, provided that there is only one mutation or deletion at a given amino acid position in the NS5A protein variant. In certain embodiments, the NS5A protein variant contains one, two, or more mutations and/or deletions, each independently selected from L23F, K24E, L28M, L28T, M28T, ΔQ30, Q30E, Q30H, Q30K, Q30R, ΔR30, R30E, R30Q, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from L23F, K24E, L28M, L28T, ΔQ30, Q30E, Q30H, Q30K, Q30R, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from L23F, K24E, M28T, ΔR30, R30E, R30Q, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from K24E, M28T, Q30E, Q30H, Q30K, Q30R, L31F, L31M, L31V, P32L, Y93C, Y93H, Y93N, E295G, and R318W, provided that there is only one mutation or deletion at a given amino acid position in the NS5A protein variant.

In certain embodiments, the HCV variant contains an NS5B protein variant. In certain embodiments, the NS5B protein variant contains a mutation or deletion. In certain embodiments, the NS5B protein variant contains one or more mutations and/or deletions at the amino acid positions of 15, 95, 96, 142, 152, 156, 222, 223, 244, 282, 309, 310, 316, 320, 321, 326, 329, 333, 365, 411, 414, 415, 423, 445, 448, 451, 452, 495, 554, 558, and 559. In certain embodiments, the NS5B protein variant contains one or more mutations and/or deletions at the amino acid positions of 316, 414, and 423. In certain embodiments, the NS5B protein variant contains one, two, or more mutations and/or deletions, each independently selected from S15G, H95Q, H95R, S96T, N142T, G152E, P156L, R222Q, C223H, C223Y, D244N, S282T, Q309R, D310N, C316N, C316S, C316Y, L320I, V321I, S326G, T329I, A333E, S365A, S365T, N411S, M414I, M414L, M414T, F415Y, M423I, M423T, M423V, C445F, Y448H, C451R, Y452H, P495A, P495I, G554D, G554S, G558R, D559G, D559N, and D559S, provided that there is only one mutation or deletion at a given amino acid position in the NS5B protein variant. In certain embodiments, the NS5B protein variant contains one, two, or more mutations and/or deletions, each independently selected from C316Y, M414T, and M423T, provided that there is only one mutation or deletion at a given amino acid position in the NS5B protein variant.

In one embodiment, provided herein is a method for treating or preventing infection caused by or associated with a hepatitis C virus variant, comprising administering to a subject a therapeutically effective amount of a compound of Formulas I or II, including a single enantiomer, a racemic mixture, a diastereomer, a mixture of diastereomers, or an isotopic variant thereof; or a pharmaceutically acceptable salt or solvate thereof.

In another embodiment, provided herein is a method for treating, preventing, or ameliorating one or more symptoms of a liver disease or disorder caused by or associated with a hepatitis C virus variant, comprising administering to a subject a therapeutically effective amount of a compound of Formulas I or II, including a single enantiomer, a racemic mixture, a diastereomer, a mixture of diastereomers, or an isotopic variant thereof or a pharmaceutically acceptable salt or solvate thereof.

In certain embodiments, the HCV variant contains an NS5A protein variant as described herein.

In one embodiment, provided herein is a method for treating or preventing infection caused by or associated with a hepatitis C virus containing an NS5A protein variant as described herein, comprising administering to a subject a therapeutically effective amount of a compound of Formulas I or II, including a single enantiomer, a racemic mixture, a diastereomer, a mixture of diastereomers, or an isotopic variant thereof or a pharmaceutically acceptable salt or solvate thereof.

In another embodiment, provided herein is a method for treating, preventing, or ameliorating one or more symptoms of a liver disease or disorder caused by or associated with hepatitis C virus containing an NS5A protein variant as described herein, comprising administering to a subject a therapeutically effective amount of a compound of Formulas I or II, including a single enantiomer, a racemic mixture, a diastereomer, a mixture of diastereomers, or an isotopic variant thereof or a pharmaceutically acceptable salt or solvate thereof.

In one embodiment, the subject is a mammal. In another embodiment, the subject is a human.

In one embodiment, provided herein is a method for inhibiting replication of a virus in a host, which comprises contacting the host with a therapeutically effective amount of a compound a compound of Formulas I or II, including a single enantiomer, a racemic mixture, a diastereomer, a mixture of diastereomers, or an isotopic variant thereof or a pharmaceutically acceptable salt or solvate thereof.

In certain embodiments, the virus is a hepatitis C virus. In certain embodiments, the virus is a drug-resistant hepatitis C virus. In certain embodiments, the virus is a hepatitis C virus variant.

In one embodiment, the hepatitis C virus is HCV genotype 1. In certain embodiments, the hepatitis C virus is HCV subtype 1a. In certain embodiments, the hepatitis C virus is HCV subtype 1b. In certain embodiments, the hepatitis C virus is HCV subtype 1c.

In another embodiment, the hepatitis C virus is HCV genotype 2. In certain embodiments, the hepatitis C virus is HCV subtype 2a. In certain embodiments, the hepatitis C virus is HCV subtype 2b. In certain embodiments, the hepatitis C virus is HCV subtype 2c.

In yet another embodiment, the hepatitis C virus is HCV genotype 3. In certain embodiments, the hepatitis C virus is HCV subtype 3a. In certain embodiments, the hepatitis C virus is HCV subtype 3b.

In yet another embodiment, the hepatitis C virus is HCV genotype 4. In certain embodiments, the hepatitis C virus is HCV subtype 4a. In certain embodiments, the hepatitis C virus is HCV subtype 4b. In certain embodiments, the hepatitis C virus is HCV subtype 4c. In certain embodiments, the hepatitis C virus is HCV subtype 4d. In certain embodiments, the hepatitis C virus is HCV subtype 4e.

In yet another embodiment, the hepatitis C virus is HCV genotype 5. In yet another embodiment, the hepatitis C virus is HCV subtype 5a.

In yet another embodiment, the hepatitis C virus is HCV genotype 6. In yet another embodiment, the hepatitis C virus is HCV subtype 6a.

In yet another embodiment, the hepatitis C virus is HCV genotype 7. In yet another embodiment, the hepatitis C virus is HCV subtype 7a.

In yet another embodiment, the hepatitis C virus is HCV genotype 8. In yet another embodiment, the hepatitis C virus is HCV subtype 8a. In yet another embodiment, the hepatitis C virus is HCV subtype 8b.

In yet another embodiment, the hepatitis C virus is HCV genotype 9. In yet another embodiment, the hepatitis C virus is HCV subtype 9a.

In yet another embodiment, the hepatitis C virus is HCV genotype 10. In yet another embodiment, the hepatitis C virus is HCV subtype 10a.

In still another embodiment, the hepatitis C virus is HCV genotype 11. In yet another embodiment, the hepatitis C virus is HCV subtype 11a.

In one embodiment, the HCV variant is a variant of HCV genotype 1. In certain embodiments, the HCV variant is a variant of HCV subtype 1a. In certain embodiments, the HCV variant is a variant of HCV subtype 1b. In certain embodiments, the HCV variant is a variant of HCV subtype 1c.

In certain embodiments, the HCV variant is a variant of HCV subtype 1a, which contains an NS5A protein variant. In certain embodiments, the NS5A protein variant contains a mutation or deletion. In certain embodiments, the NS5A protein variant contains one or more mutations and/or deletions at the amino acid positions of 28, 30, 31, 32, 54, and 93. In certain embodiments, the NS5A protein variant contains one or more mutations and/or deletions at the amino acid positions of 23, 24, 28, 30, 31, 32, 37, 54, 58, 63, 93, 295, 318, 320, 356, 404, and 442. In certain embodiments, the NS5A protein variant contains one or more mutations and/or deletions at the amino acid positions of 24, 28, 30, 31, 32, 54, 93, 295, and 318. In certain embodiments, the NS5A protein variant contains one, two, or more mutations and/or deletions, each independently selected from M28T, ΔQ30, Q30E, Q30H, Q30K, Q30R, L31F, L31M, L31V, P32L, H54Y, Y93C, Y93H, and Y93N, provided that there is only one mutation or deletion at a given amino acid position in the NS5A protein variant. In certain embodiments, the NS5A protein variant contains one, two, or more mutations and/or deletions, each independently selected from L23F, K24E, L28M, L28T, M28T, ΔQ30, Q30E, Q30H, Q30K, Q30R, ΔR30, R30E, R30Q, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from L23F, K24E, L28M, L28T, ΔQ30, Q30E, Q30H, Q30K, Q30R, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from L23F, K24E, M28T, ΔR30, R30E, R30Q, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from K24E, M28T, Q30E, Q30H, Q30K, Q30R, L31F, L31M, L31V, P32L, Y93C, Y93H, Y93N, E295G, and R318W, provided that there is only one mutation or deletion at a given amino acid position in the NS5A protein variant. In certain embodiments, the NS5A protein variant contains one or more mutations at the amino acid positions of 28, 30, 31, 32, and 93. In certain embodiments, the NS5A protein variant contains one, two, or more mutations, each independently selected from M28T, Q30E, Q30H, Q30K, Q30R, L31F, L31M, L31V, P32L, Y93C, Y93H, and Y93N, provided that there is only one mutation at a given amino acid position in the NS5A protein variant. In certain embodiments, the NS5A protein variant contains one or more mutations at the amino acid positions of 24, 28, 30, 31, 32, 93, 295, and 318. In certain embodiments, the NS5A protein variant contains one, two, or more mutations, each independently selected from K24E, M28T, Q30E, Q30H, Q30K, Q30R, L31F, L31M, L31V, P32L, Y93C, Y93H, Y93N, E295G, and R318W, provided that there is only one mutation at a given amino acid position in the NS5A protein variant.

In certain embodiments, the HCV variant is a variant of HCV subtype 1b, which contains an NS5A protein variant. In certain embodiments, the NS5A protein variant contains a mutation or deletion. In certain embodiments, the NS5A protein variant contains one or more mutations and/or deletions at the amino acid positions of 23, 28, 30, 31, 32, 37, 54, 58, 63, and 93. In certain embodiments, the NS5A protein variant contains one or more mutations and/or deletions at the amino acid positions of 23, 24, 28, 30, 31, 32, 37, 54, 58, 63, 93, 295, 318, 320, 356, 404, and 442. In certain embodiments, the NS5A protein variant contains one or more mutations and/or deletions at the amino acid positions of 24, 28, 30, 31, 32, 54, 93, 295, and 318. In certain embodiments, the NS5A protein variant contains one, two, or more mutations and/or deletions, each independently selected from L23F, L28M, L28T, ΔR30, R30E, R30Q, L31F, L31M, L31V, P32L, F37L, Q54H, P58H, P58S, I63V, Y93C, Y93H, Y93N, and Y93S, provided that there is only one mutation or deletion at a given amino acid position in the NS5A protein variant. In certain embodiments, the NS5A protein variant contains one, two, or more mutations and/or deletions, each independently selected from L23F, K24E, L28M, L28T, M28T, ΔQ30, Q30E, Q30H, Q30K, Q30R, ΔR30, R30E, R30Q, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from L23F, K24E, L28M, L28T, ΔQ30, Q30E, Q30H, Q30K, Q30R, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from L23F, K24E, M28T, ΔR30, R30E, R30Q, L31F, L31M, L31V, P32L, F37L, H54Y, Q54H, P58H, P58S, I63V, Y93C, Y93H, Y93N, Y93S, E295G, R318W, D320E, R356Q, G404S, and E442G, provided that there is only one mutation or deletion at a given amino acid position in the NS5A protein variant. In certain embodiments, the NS5A protein variant contains one, two, or more mutations and/or deletions, each independently selected from K24E, M28T, Q30E, Q30H, Q30K, Q30R, L31F, L31M, L31V, P32L, Y93C, Y93H, Y93N, E295G, and R318W, provided that there is only one mutation or deletion at a given amino acid position in the NS5A protein variant. In certain embodiments, the NS5A protein variant contains one or more mutations at the amino acid positions of 28, 30, 31, 32, and 93. In certain embodiments, the NS5A protein variant contains one, two, or more mutations, each independently selected from L28T, R30E, L31F, L31M, L31V, P32L, Y93C, Y93H, and Y93N, provided that there is only one mutation at a given amino acid position in the NS5A protein variant. In certain embodiments, the NS5A protein variant contains one or more mutations at the amino acid positions of 24, 28, 30, 31, 32, 93, 295, and 318. In certain embodiments, the NS5A protein variant contains one, two, or more mutations, each independently selected from K24E, M28T, Q30E, Q30H, Q30K, Q30R, L31F, L31M, L31V, P32L, Y93C, Y93H, Y93N, E295G, and R318W, provided that there is only one mutation at a given amino acid position in the NS5A protein variant.

In another embodiment, the HCV variant is a variant of HCV genotype 2. In certain embodiments, the HCV variant is a variant of HCV subtype 2a. In certain embodiments, the HCV variant is a variant of HCV subtype 2b. In certain embodiments, the HCV variant is a variant of HCV subtype 2c.

In yet another embodiment, the HCV variant is a variant of HCV genotype 3. In certain embodiments, the HCV variant is a variant of HCV subtype 3a. In certain embodiments, the HCV variant is a variant of HCV subtype 3b.

In yet another embodiment, the HCV variant is a variant of HCV genotype 4. In certain embodiments, the HCV variant is a variant of HCV subtype 4a. In certain embodiments, the HCV variant is a variant of HCV subtype 4b. In certain embodiments, the HCV variant is a variant of HCV subtype 4c. In certain embodiments, the HCV variant is a variant of HCV subtype 4d. In certain embodiments, the HCV variant is a variant of HCV subtype 4e.

In yet another embodiment, the HCV variant is a variant of HCV genotype 5. In yet another embodiment, the HCV variant is a variant of HCV subtype 5a.

In yet another embodiment, the HCV variant is a variant of HCV genotype 6. In yet another embodiment, the HCV variant is a variant of HCV subtype 6a.

In yet another embodiment, the HCV variant is a variant of HCV genotype 7. In yet another embodiment, the HCV variant is a variant of HCV subtype 7a.

In yet another embodiment, the HCV variant is a variant of HCV genotype 8. In yet another embodiment, the HCV variant is a variant of HCV subtype 8a. In yet another embodiment, the HCV variant is a variant of HCV subtype 8b.

In yet another embodiment, the HCV variant is a variant of HCV genotype 9. In yet another embodiment, the HCV variant is a variant of HCV subtype 9a.

In yet another embodiment, the HCV variant is a variant of HCV genotype 10. In yet another embodiment, the HCV variant is a variant of HCV subtype 10a.

In still another embodiment, the HCV variant is a variant of HCV genotype 11. In yet another embodiment, the HCV variant is a variant of HCV subtype 11a.

In certain embodiments, provided herein is a method for inhibiting replication of hepatitis C virus containing an NS5A protein variant in a host, which comprises administering to the host a therapeutically effective amount of a compound of Formulas I or II, including a single enantiomer, a racemic mixture, a diastereomer, a mixture of diastereomers, or an isotopic variant thereof; or a pharmaceutically acceptable salt or solvate thereof.

In one embodiment, the host is a cell. In another embodiment, the host is a human cell. In yet another embodiment, the host is a mammal. In still another embodiment, the host is human.

In certain embodiments, administration of a therapeutically effective amount of a compound of Formulas I or II, including a single enantiomer, a racemic mixture, a diastereomer, a mixture of diastereomers, or an isotopic variant thereof or a pharmaceutically acceptable salt or solvate thereof) results in a 10%, 20%, 30%, 40%, 50%, 60%, 70%, 80%, 90%, 95%, 99% or more reduction in the replication of the virus relative to a subject without administration of the compound, as determined at 1 day, 2 days, 3 days, 4 days, 5 days, 10 days, 15 days, or 30 days after the administration by a method known in the art, e.g., determination of viral titer.

In certain embodiments, administration of a therapeutically effective amount of a compound of Formulas I or II, including a single enantiomer, a racemic mixture, a diastereomer, a mixture of diastereomers, or an isotopic variant thereof or a pharmaceutically acceptable salt or solvate thereof) results in a 1, 2, 3, 4, 5, 10, 15, 20, 25, 50, 75, 100-fold or more reduction in the replication of the virus relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound of Formulas I or II, including a single enantiomer, a racemic mixture, a diastereomer, a mixture of diastereomers, or an isotopic variant thereof or a pharmaceutically acceptable salt or solvate thereof) results in a 10%, 20%, 30%, 40%, 50%, 60%, 70%, 80%, 90%, 95%, 99% or more reduction in the viral titer relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound of Formulas I or II, including a single enantiomer, a racemic mixture, a diastereomer, a mixture of diastereomers, or an isotopic variant thereof; or a pharmaceutically acceptable salt or solvate thereof) results in a 1, 2, 3, 4, 5, 10, 15, 20, 25, 50, 75, 100 or more fold reduction in the viral titer relative to a subject without administration of the compound, as determined at 1 day, 2 days, 3 days, 4 days, 5 days, 10 days, 15 days, or 30 days after the administration by a method known in the art.

In certain embodiments, provided herein is a method for inhibiting the replication of an HCV virus, which comprises contacting the virus with a therapeutically effective amount of a compound a compound of Formulas I or II, including a single enantiomer, a racemic mixture, a diastereomer, a mixture of diastereomers, or an isotopic variant thereof; or a pharmaceutically acceptable salt or solvate thereof.

In certain embodiments, the contacting of the virus with a therapeutically effective amount of a compound of Formulas I or II, including a single enantiomer, a racemic mixture, a diastereomer, a mixture of diastereomers, or an isotopic variant thereof; or a pharmaceutically acceptable salt or solvate thereof) results in a 10%, 20%, 30%, 40%, 50%, 60%, 70%, 80%, 90%, 95%, 99% or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the virus with a therapeutically effective amount of a compound of Formulas I or II, including a single enantiomer, a racemic mixture, a diastereomer, a mixture of diastereomers, or an isotopic variant thereof; or a pharmaceutically acceptable salt or solvate) results in a 1, 2, 3, 4, 5, 10, 15, 20, 25, 50, 75, 100 or more fold reduction in the viral titer relative to the virus without such contact, as determined at 1 day, 2 days, 3 days, 4 days, 5 days, 10 days, 15 days, or 30 days after the initial contact, by a method known in the art.

In still another embodiment, provided herein is a method for treating, preventing, or ameliorating one or more symptoms of a liver disease or disorder associated with an HCV infection, comprising administering to a subject a therapeutically effective amount of the compound a compound of Formulas I or II, including a single enantiomer, a racemic mixture, a diastereomer, a mixture of diastereomers, or an isotopic variant thereof or a pharmaceutically acceptable salt or solvate thereof. Non-limiting examples of diseases associated with HCV infection include chronic hepatitis, cirrhosis, hepatocarcinoma, or extra hepatic manifestation.

Depending on the condition, disorder, or disease, to be treated and the subject's condition, a compound provided herein may be administered by oral, parenteral (e.g., intramuscular, intraperitoneal, intravenous, intracerebroventricular (ICV), intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1,000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.

The compounds provided herein may also be combined or used in combination with other therapeutic agents useful in the treatment and/or prevention of an HCV infection.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to prevent, treat, or manage a condition, disorder, or disease, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a condition, disorder, or disease. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, treatment, or management of a condition, disorder, or disease). In addition, a synergistic effect can result in improved efficacy of agents in the prevention, treatment, or management of a condition, disorder, or disease. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent, such as an anti-HCV agent. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of HCV can emerge after prolonged treatment with an antiviral agent. Drug resistance most typically occurs due to the mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameters of the drug can be altered by such combination or alternation therapy. In general, combination therapy is typically preferred over alternation therapy because it induces multiple simultaneous stresses on the virus.

In certain embodiments, the pharmaceutical compositions provided herein further comprise a second antiviral agent as described herein. In certain embodiments, the compound provided herein is combined with one or more agents selected from an interferon, ribavirin, amantadine, an interleukin, an NS3 protease inhibitor, a cysteine protease inhibitor, a phenanthrenequinone, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, or a ribozyme. In one embodiment, the second antiviral agent is an interferon. In another embodiment, the interferon is selected from pegylated interferon alpha 2a, interferon alfacon-1, natural interferon, ALBUFERON®, interferon beta-1a, omega interferon, interferon alpha, interferon gamma, interferon tau, interferon delta, or interferon gamma-1b.

In certain embodiments, the compound provided herein is combined with an HCV protease inhibitor, including, but not limited to, BI 201335 (Boehringer Ingelheim); TMC 435 or TMC 435350 (Medivir/Tibotec); ITMN 191/R7227 (InterMune); MK 7009 (Merck); SCH 5034/SCH 503034/Boceprevir and SCH 900518/narlaprevir (Schering); VX950/telaprevir (Vertex); substrate-based NS3 protease inhibitors as disclosed in DE 19914474, WO 98/17679, WO 98/22496, WO 99/07734, and Attwood et al., *Antiviral Chemistry and Chemotherapy* 1999, 10, 259-273; non-substrate-based NS3 protease inhibitors, including 2,4,6-trihydroxy-3-nitro-benzamide derivatives (Sudo et al., *Biochem. Biophys. Res. Commun.* 1997, 238, 643-647), a phenanthrenequinone (Chu et al., *Tetrahedron Letters* 1996, 37, 7229-7232), RD3-4082, RD3-4078, SCH 68631, and SCH 351633 (Chu et al., *Bioorganic and Medicinal Chemistry Letters* 1999, 9, 1949-1952); and Eglin C, a potent serine protease inhibitor (Qasim et al., *Biochemistry* 1997, 36, 1598-1607).

Other suitable protease inhibitors for the treatment of HCV include those disclosed in, for example, U.S. Pat. No. 6,004,933, which discloses a class of cysteine protease inhibitors of HCV endopeptidase 2.

Additional hepatitis C virus NS3 protease inhibitors include those disclosed in, for example, Llinàs-Brunet et al., *Bioorg. Med. Chem. Lett.* 1998, 8, 1713-1718; Steinkühler et al., *Biochemistry* 1998, 37, 8899-8905; U.S. Pat. Nos. 5,538,865; 5,990,276; 6,143,715; 6,265,380; 6,323,180; 6,329,379; 6,410,531; 6,420,380; 6,534,523; 6,608,027; 6,642,204; 6,653,295; 6,727,366; 6,838,475; 6,846,802; 6,867,185; 6,869,964; 6,872,805; 6,878,722; 6,908,901; 6,911,428; 6,995,174; 7,012,066; 7,041,698; 7,091,184; 7,169,760; 7,176,208; 7,208,600; and 7,491,794; U.S. Pat. Appl. Publ. Nos.: 2002/0016294, 2002/0016442; 2002/0032175; 2002/0037998; 2004/0229777; 2005/0090450; 2005/0153877; 2005/176648; 2006/0046956; 2007/0021330; 2007/0021351; 2007/0049536; 2007/0054842; 2007/0060510; 2007/0060565; 2007/0072809; 2007/0078081; 2007/0078122; 2007/0093414; 2007/0093430; 2007/0099825; 2007/0099929; 2007/0105781, 2008/0152622, 2009/0035271, 2009/0035272, 2009/0047244, 2009/0111969, 2009/0111982, 2009/0123425, 2009/0130059, 2009/0148407, 2009/0156800, 2009/0169510, 2009/0175822, 2009/0180981, and 2009/0202480; U.S. Pat. application Ser. No. 12/365,127; and International Pat. Appl. Publ. Nos.: WO 98/17679; WO 98/22496; WO 99/07734; WO 00/09543; WO 00/59929; WO 02/08187; WO 02/08251; WO 02/08256; WO 02/08198; WO 02/48116; WO 02/48157; WO 02/48172; WO 02/60926; WO 03/53349; WO 03/64416; WO 03/64455; WO 03/64456; WO 03/66103; WO 03/99274; WO 03/99316; WO 2004/032827; WO 2004/043339; WO 2005/037214; WO 2005/037860; WO 2006/000085; WO 2006/119061; WO 2006/122188; WO 2007/001406; WO 2007/014925; WO 2007/014926; WO 2007/015824; WO 2007/056120, WO 2008/019289, WO 2008/021960, WO 2008/022006, WO 2008/086161, WO 2009/053828, WO 2009/058856, WO 2009/073713, WO 2009/073780, WO 2009/080542, WO 2009/082701, WO 2009/082697, and WO 2009/085978; the disclosure of each of which is incorporated herein by reference in its entirety.

Other protease inhibitors include thiazolidine derivatives, such as RD-1-6250, RD4 6205, and RD4 6193, which show relevant inhibition in a reverse-phase HPLC assay with an NS3/4A fusion protein and NS5A/5B substrate (Sudo et al., *Antiviral Research* 1996, 32, 9-18); and thiazolidines and benzanilides identified in Kakiuchi et al., *FEBS Lett.* 1998, 421, 217-220; and Takeshita et al., *Analytical Biochemistry* 1997, 247, 242-246.

Suitable helicase inhibitors include, but are not limited to, those disclosed in U.S. Pat. No. 5,633,358; and International Pat. Appl. Publ. No. WO 97/36554.

Suitable nucleotide polymerase inhibitors include, but are not limited to, gliotoxin (Ferrari et al., *Journal of Virology* 1999, 73, 1649-1654) and cerulenin (Lohmann et al., *Virology* 1998, 249, 108-118).

Suitable interfering RNA (iRNA) based antivirals include, but are not limited to, short interfering RNA (siRNA) based antivirals, such as Sirna-034 and those described in International Pat. Appl. Publ. Nos. WO/03/070750 and WO 2005/012525, and U.S. Pat. Appl. Publ. No. 2004/0209831.

Suitable antisense phosphorothioate oligodeoxynucleotides (S-ODN) complementary to sequence stretches in the 5' non-coding region (NCR) of HCV virus include, but are not limited to those described in Alt et al., *Hepatology* 1995, 22, 707-717, and nucleotides 326-348 comprising the 3' end of the NCR and nucleotides 371-388 located in the core coding region of HCV RNA (Alt et al., *Archives of Virology* 1997, 142, 589-599; and Galderisi et al., *Journal of Cellular Physiology* 1999, 181, 251-257);

Suitable inhibitors of IRES-dependent translation include, but are not limited to, those described in Japanese Pat. Appl. Publ. Nos.: JP 08268890 and JP 10101591.

Suitable ribozymes include those disclosed in, for example, U.S. Pat. Nos. 6,043,077; 5,869,253; and 5,610,054.

Suitable nucleoside analogs include, but are not limited to, the compounds described in U.S. Pat. Nos. 6,660,721; 6,777,395; 6,784,166; 6,846,810; 6,927,291; 7,094,770; 7,105,499; 7,125,855; and 7,202,224; U.S. Pat. Appl. Publ. Nos. 2004/0121980; 2005/0009737; 2005/0038240; and 2006/0040890; and International Pat. Appl. Publ. Nos: WO 99/43691; WO 01/32153; WO 01/60315; WO 01/79246; WO 01/90121, WO 01/92282, WO 02/18404; WO 02/32920, WO 02/48165, WO 02/057425; WO 02/057287; WO 2004/002422, WO 2004/002999, and WO 2004/003000.

Other miscellaneous compounds that can be used as second agents include, for example, 1-amino-alkylcyclohexanes (U.S. Pat. No. 6,034,134), alkyl lipids (U.S. Pat. No. 5,922,757), vitamin E and other antioxidants (U.S. Pat. No. 5,922,757), squalene, amantadine, bile acids (U.S. Pat. No. 5,846,964), N-(phosphonacetyl)-L-aspartic acid (U.S. Pat. No. 5,830,905), benzenedicarboxamides (U.S. Pat. No. 5,633,388), polyadenylic acid derivatives (U.S. Pat. No. 5,496,546), 2',3'-dideoxyinosine (U.S. Pat. No. 5,026,687), benzimidazoles (U.S. Pat. No. 5,891,874), plant extracts (U.S. Pat. Nos. 5,725,859; 5,837,257; and 6,056,961), and piperidines (U.S. Pat. No. 5,830,905).

In certain embodiments, one or more compounds provided herein are administered in combination or alternation with an anti-hepatitis C virus interferon, including, but not limited to, INTRON® A (interferon alfa-2b), PEGASYS® (Peginterferon alfa-2a) ROFERON® A (recombinant interferon alfa-2a), INFERGEN® (interferon alfacon-1), and PEG-INTRON® (pegylated interferon alfa-2b). In one embodiment, the anti-hepatitis C virus interferon is INFERGEN®, IL-29 (PEG-Interferon lambda), R7025 (Maxy-alpha), BELEROFON®, oral interferon alpha, BLX-883 (LOCTERON®), omega interferon, MULTIFERON®, medusa interferon, ALBUFERON®, or REBIF®.

In certain embodiments, one or more compounds provided herein are administered in combination or alternation with an anti-hepatitis C virus polymerase inhibitor, such as ribavirin, viramidine, NM 283 (valopicitabine), PSI-6130, R1626, HCV-796, R7128, and those as disclosed in U.S. Pat. Appl. Publ. Nos. 2009/0081158 and 2009/0238790, the disclosure of each of which is incorporated herein by reference in its entirety.

In certain embodiments, the one or more compounds provided herein are administered in combination with ribavirin and an anti-hepatitis C virus interferon, such as INTRON® A (interferon alfa-2b), PEGASYS® (Peginterferon alfa-2a), ROFERON® A (recombinant interferon alfa-2a), INFERGEN® (interferon alfacon-1), and PEG-INTRON® (pegylated interferon alfa-2b), In certain embodiments, one or more compounds provided herein are administered in combination or alternation with an anti-hepatitis C virus protease inhibitor, such as GS-9451, ITMN-191, SCH 503034, VX950 (telaprevir), and TMC 435.

In certain embodiments, one or more compounds provided herein are administered in combination or alternation with an anti-hepatitis C virus vaccine, including, but not limited to, TG4040, PEVIPRO™, CGI-5005, HCV/MF59, GV1001, IC41, and INNO0101 (E1).

In certain embodiments, one or more compounds provided herein are administered in combination or alternation with an anti-hepatitis C virus monoclonal antibody, such as AB68 and XTL-6865 (formerly HepX-C); or an anti-hepatitis C virus polyclonal antibody, such as cicavir.

In certain embodiments, one or more compounds provided herein are administered in combination or alternation with an anti-hepatitis C virus immunomodulator, such as ZADAXIN® (thymalfasin), NOV-205, and oglufanide.

In certain embodiments, one or more compounds provided herein are administered in combination or alternation with NEXAVAR®, doxorubicin, PI-88, amantadine, JBK-122, VGX-410C, MX-3253 (celgosivir), SUVUS® (BIVN-401 or virostat), PF-03491390 (formerly IDN-6556), G126270, UT-231B, DEBIO-025, EMZ702, ACH-0137171, MitoQ, ANA975, AVI-4065, bavituximab (tarvacin), ALINIA® (nitrazoxanide), GS-9620, and PYN17.

The compounds provided herein can also be administered in combination with other classes of compounds, including, but not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound a compound of Formulas I or II, including a single enantiomer, a racemic mixture, a diastereomer, a mixture of diastereomers, or an isotopic variant thereof; or a pharmaceutically acceptable salt or solvate thereof.

In certain embodiments, the kit includes a container comprising a dosage form of the compound a compound of Formulas I or II, including a single enantiomer, a racemic mixture, a diastereomer, a mixture of diastereomers, or an isotopic variant thereof; or a pharmaceutically acceptable salt or solvate thereof, in a container comprising one or more other therapeutic agent(s) described herein.

Kits provided herein can further include devices that are used to administer the active ingredients. Examples of such devices include, but are not limited to, syringes, needleless injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples. As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL, (microliters); L (liter); mM (millimolar); μM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); HPLC (high-performance liquid chromatography or high pressure liquid chromatography); DCM (dichloromethane); DMF (N,N-dimethylformamide); EtOAc (ethyl acetate); THF (tetrahydrofuran); DIPEA (N,N-diisopropylethylamine); TEA (tri ethyl amine); TFA (trifluoroacetic acid); HATU (2-(7-aza-1H-benzotriazole-1-yl)-1,1,3,3-tetramethyluronium hexafluorophosphate); Me (methyl); Et (ethyl); and Pd(dppf)Cl$_2$ ((1,1'-bis(diphenylphosphino)ferrocene) dichloropalladium(II); TLC (thin-layer chromatography); TFAA (trifluoroacetic acid); EA (ethyl acetate).

Methods for Making the Compounds of Formulas (I) or (II)

The Compounds of Formulas (I) or (II) may be prepared from known or readily prepared starting materials, following methods known to one skilled in the art of organic synthesis. Methods useful for making the Compounds of Formulas (I) or (II) are set forth in the Examples below and generalized in Scheme 1 below. Alternative synthetic pathways and analogous structures will be apparent to those skilled in the art of organic synthesis.

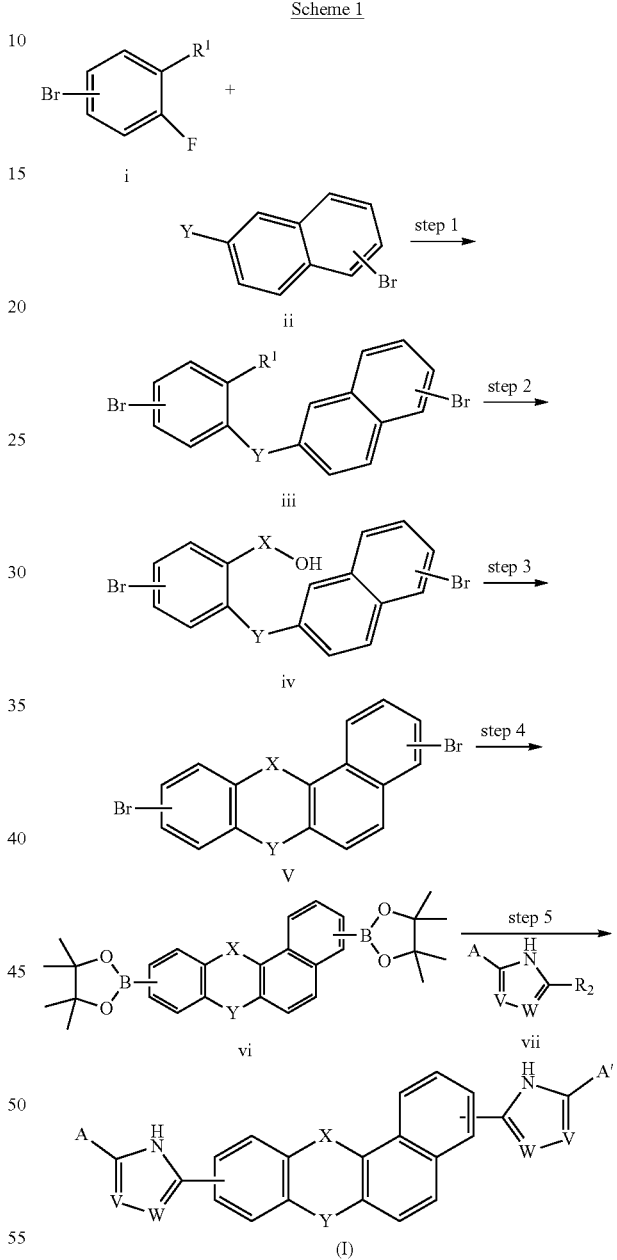

Compound i is commercially available or prepared according to well known procedures. Examples of R$^1$ include CN, methyl ester, and other moieties having similar functionality. Examples of Y include hydroxyl, thiol, and amines. Substitution of the fluorine of compound i by the Y group of compound ii under basic condition leads to the formation of compound iii. R$^1$ is converted to X—OH, which may be anacid, substituted alcohol, or other moiety having similar functionality. Compound iv undergoes ring closure in the presence of TFAA, AlCl$_3$, or other similar reagents to give compound v. When X is a carbonyl group (—CO—), it can be further functionalized to other groups, such as —CH(CH$_3$)—, by using known chemistry. Compound v is converted to di-boronic ester vi under Pd catalyzed conditions or other similar conditions. Compound I is obtained by Pd catalyzed reaction between compound vi and vii. The preparation of vii is well described in the literature.

Compound of formulas (II) can prepared by similar chemistry as outlined in Scheme 1 starting with correspondingly different staring materials.

Compounds of Formulas (I) or (II) may be further elaborated using methods that would be well-known to those skilled in the art of organic synthesis or, for example, the methods described in the Examples below, to make the full scope of the Compounds of Formulas (I) or (II).

One skilled in the art of organic synthesis will recognize that the synthesis of compounds with multiple reactive functional groups, such as —OH and NH$_2$, may require protection of certain functional group for the purpose of chemical compatibility with a particular reaction condition. Suitable protecting groups for the various functional groups of these compounds and methods for their installation and removal are well known in the art of organic chemistry. A summary of many of these methods can be found in Greene et al., supra.

One skilled in the art of organic synthesis will also recognize that one route for the synthesis of the Compounds of Formulas (I) or (II) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

The starting materials used and the intermediates prepared using the methods set forth in Scheme 1 may be isolated and purified if desired using conventional techniques, including but not limited to filtration, distillation, crystallization, chromatography and the like. Such materials can be characterized using conventional means, including physical constants and spectral data.

Preparation of Intermediate Compounds

Intermediate Compound Cap1

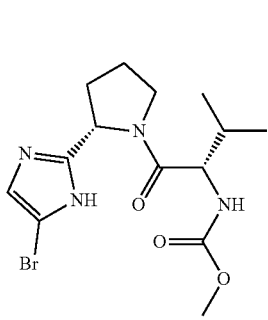

cap 1

Compound cap1 was prepared in Example 7 of WO2012041014.

Intermediate Compound Cap2

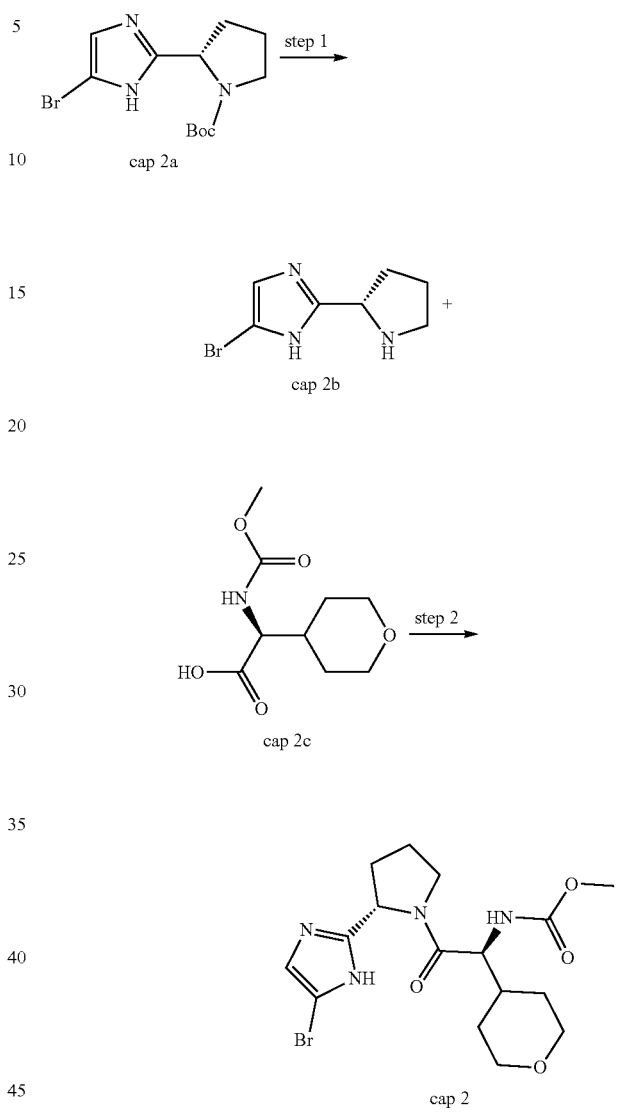

Step 1

Compound cap 2a was prepared in Example 7 of WO 2012/040923 A1. Compound cap 2a (50 g, 0.16 mmol) was added into TFA/DCM (1:1, 10 mL). The mixture was stirred at 25° C. for 2 hours; then concentrated and dried under high vacuum to give to desired product cap 2b (34.4 g, 100% yield). LC/MS: Anal. Calcd. For [M+H]$^+$ C$_7$H$_{10}$BrN$_3$: 216.01; found 216.1.

Step 2

Compound cap 2c was prepared in Example 4 of WO 2012/040923 A1. To a mixture of cap 2b (1.9 g, 9 mmol), cap 2c (1.9 g, 9 mmol) and DIPEA (4 mL) in CH$_2$Cl$_2$ (5 mL) was added HATU reagent (3.5 g, 9 mmol). The resulting mixture was stirred at 25° C. for 2 hours. The reaction mixture was concentrated, then purified by SiO$_2$ chromatography (eluent: petroleum ether/ethyl acetate=5:1 to 1:2) to give the compound cap 2. LC/MS: Anal. Calcd. For [M+H]$^+$ C$_{16}$H$_{23}$BrN$_4$O$_4$: 415.09, 417.09; found 415.1, 417.1.

35
Intermediate Compound Cap3

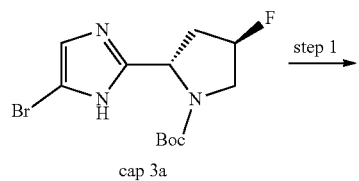
cap 3a

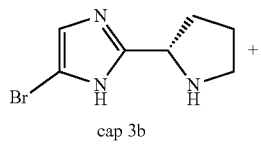
cap 3b

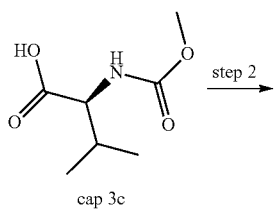
cap 3c

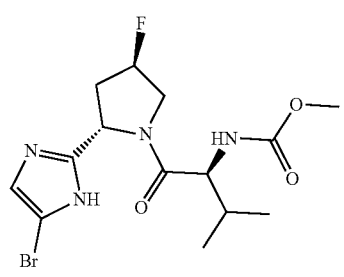
cap 3

Step 1

Compound cap 3a was prepared in Example 10 of WO2012041014 A1. Compound cap 3a (50 g, 0.16 mmol) was added into TFA/DCM (1:1, 10 mL). The mixture was stirred at 25° C. for 2 hours; then concentrated and dried under high vacuum to give to desired product cap 3b (34.4 g, 100% yield). LC/MS: Anal. Calcd. For [M+H]$^+$ C$_7$H$_{10}$BrN$_3$: 216.01; found 216.1.

Step 2

Compound cap 3c was prepared in Example 4 of WO 2012/040923 A1. To a mixture of cap 3b (1.9 g, 9 mmol), cap 3c (1.9 g, 9 mmol) and DIPEA (4 mL) in CH$_2$Cl$_2$ (5 mL) was added HATU reagent (3.5 g, 9 mmol). The resulting mixture was stirred at 25° C. for 2 hours. The reaction mixture was concentrated, then purified by SiO$_2$ chromatography (eluent: petroleum ether/ethyl acetate=5:1 to 1:2) to give the compound cap 3. LC/MS: Anal. Calcd. For [M+H]$^+$ C$_{16}$H$_{23}$BrN$_4$O$_4$: 415.09, 417.09; found 415.1, 417.1.

36
Intermediate Compound Cap4

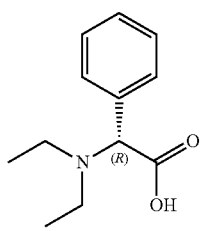
cap 4

Step 1

Compound cap 4 was prepared in Example cap-2 of WO 2008144380A1.

Intermediate Compound 2,9-dibromo-6-fluoro-12H-benzo[b]xanthen-12-one

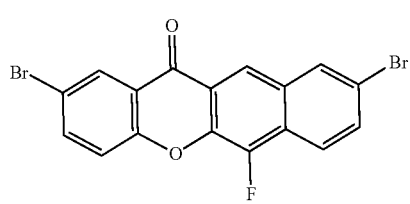 [SMILES: O=c1c2cc(Br)ccc2oc2c(F)c3ccc(Br)cc3cc12]

2,9-dibromo-6-fluoro-12H-benzo[b]xanthen-12-one

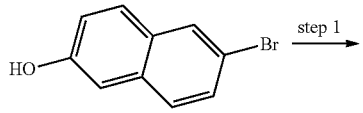

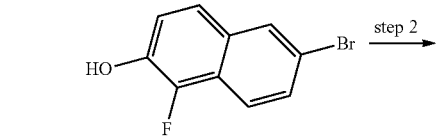

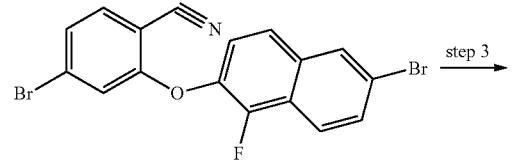

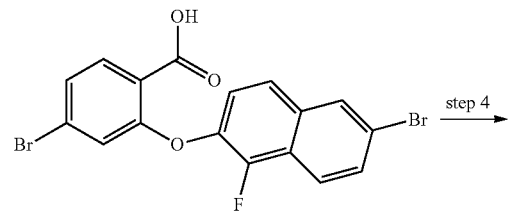

-continued

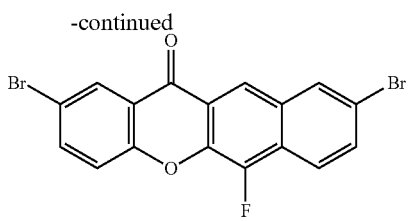

Step 1

6-bromonaphthalen-2-ol (5 g, 22.41 mmol) was dissolved in DMF (50 mL) in a 250 mL flask. N-fluorobenzenesulfonimide (21.20 g, 67.2 mmol) was added and the solution was stirred at 25° C. for 2 days. The solution was concentrated. The residue was purified by column chromatography on silica gel (120 g), eluting with Hexane and EtOAc (0% to 50%) to give 6-bromo-1-fluoronaphthalen-2-ol (6.1 g, purity: 88%, yield: 99%).

Step 2

5-bromo-2-fluorobenzonitrile (2.293 g, 11.46 mmol), 6-bromo-1-fluoronaphthalen-2-ol (3.14 g, 11.46 mmol), and Cs2CO3 (7.47 g, 22.93 mmol) were added into a 500 ML flask. DMF (115 ml) was added. The solution was stirred at 80° C. for 24 hours. EtOAc (150 mL) and water (100 mL) were added. The organic layer was separated and washed with water (100 mL×2), brine, dried over anhydrous $Na_2SO_4$, filtered and concentrated. The product was purified by $SiO_2$ chromatography (120 g, Hexane/EtOAc 0% to 50%) to give 4-bromo-2-((6-bromo-1-fluoronaphthalen-2-yl)oxy)benzonitrile (4.25 g, 88%). LCMS: 424.0 $[M+H]^+$ Step 3

4-bromo-2-((6-bromo-1-fluoronaphthalen-2-yl)oxy)benzonitrile (2 g, 4.75 mmol) was dissolved in Ethanol (23.75 ml). NaOH (19.00 ml, 47.5 mmol) was added. The solution was stirred at 85° C. for 20 hours. After cooling down, TLC indicated staring material disappeared. The solution was poured into 100 mL 6N HCl with good stirring. The solid was collected by filtration, washed with water and dried at 50° C. under vacuum for overnight to give crude 4-bromo-2-((6-bromo-1-fluoronaphthalen-2-yl)oxy)benzoic acid. To this crude material was added CH2Cl2 (15 mL) and the suspension was stirred at RT for 20 minutes. The solid was collected by filtration and washed with CH2Cl2, dried under vacuum for overnight to 4-bromo-2-((6-bromo-1-fluoronaphthalen-2-yl)oxy)benzoic acid batch 1 (435 mg). The filtrate was concentrated and stirred with 7 mL CH2Cl2. The solid was collected by filtration to give 4-bromo-2-((6-bromo-1-fluoronaphthalen-2-yl)oxy)benzoic acid batch 2 (150 mg). LCMS: 460.9, 462.9 $[M+Na]^+$ Step 4

4-bromo-2-((6-bromo-1-fluoronaphthalen-2-yl)oxy)benzoic acid (172 mg, 0.391 mmol) and CH2Cl2 (1954 μl) were added into a 40 mL flask and cooled to 0° C. TFAA (66.2 μl, 0.469 mmol) was added via syringe and the solution was stirred at 0° C. for 30 min. Then BF3.OEt2 (9.91 μl, 0.078 mmol) was added via syringe and the solution was stirred at 0° C. for 30 min, then at 25° C. for 16 hours. A suspension was formed. The solid was collected by filtration to give 2,9-dibromo-6-fluoro-12H-benzo[b]xanthen-12-one. LCMS: 442.9 $[M+Na]^+$ Intermediate Compound
3,9-dibromo-12H-benzo[a]xanthen-12-one

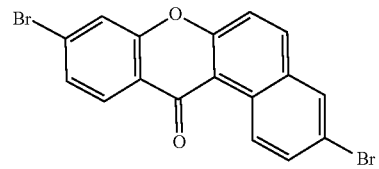 [SMILES: O=c1c2ccc(Br)cc2oc2ccc3cc(Br)ccc3c12]

3,9-dibromo-12H-benzo[a]xanthen-12-one

Step 1

4-bromo-2-fluorobenzonitrile (5 g, 25.00 mmol), 6-bromonaphthalen-2-ol (5.58 g, 25.00 mmol), and cesium carbonate (16.29 g, 50.0 mmol) were added into a 500 ML flask. DMF (250 ml) was added. The solution was stirred at 80° C. for 24 hours. EtOAc (350 mL) and water (200 mL) were added. The organic layer was separated and washed with water (150 mL×2), brine, dried over anhydrous $Na_2SO_4$, filtered and concentrated. The product was dried under vacuum for 2 hours and was used without further purification.

Step 2

4-bromo-2-((6-bromonaphthalen-2-yl)oxy)benzonitrile (8.5 g, 21.09 mmol) was dissolved in Ethanol (105 ml). NaOH (84 ml, 211 mmol) was added. The solution was stirred at 85° C. for 20 hours. After cooling down, TLC indicated starting material disappeared. The solution was poured into 200 mL 6N HCl with good stirring. The solid was collected by filtration, washed with water and dried at 50° C. under vacuum for overnight to give 4-bromo-2-((6-bromonaphthalen-2-yl)oxy)benzoic acid (8.6 g, 97%). LCMS: 422.9 $[M+H]^+$ Step 3

4-bromo-2-((6-bromonaphthalen-2-yl)oxy)benzoic acid (500 mg, 1.185 mmol) and CH2Cl2 (5923 µl) were added into a 40 mL flask and cooled to 0° C. TFAA (201 µl, 1.422 mmol) was added via syringe and the solution was stirred at 0° C. for 30 min. Then BF3.OEt2 (15.01 µl, 0.118 mmol) was added via syringe and the solution was stirred at 0° C. for 30 min, then at 25° C. for 2 hours. A suspension was formed. NaOH (1N, 10 mL) was added and stirred at RT for 10 min. The solid was collected by filtration, washed with water twice, and dried under vacuum at 50° C. for overnight to give 3,9-dibromo-12H-benzo[a]xanthen-12-one. LCMS: 405.0 [M+H]$^+$ Preparation of Compound 3

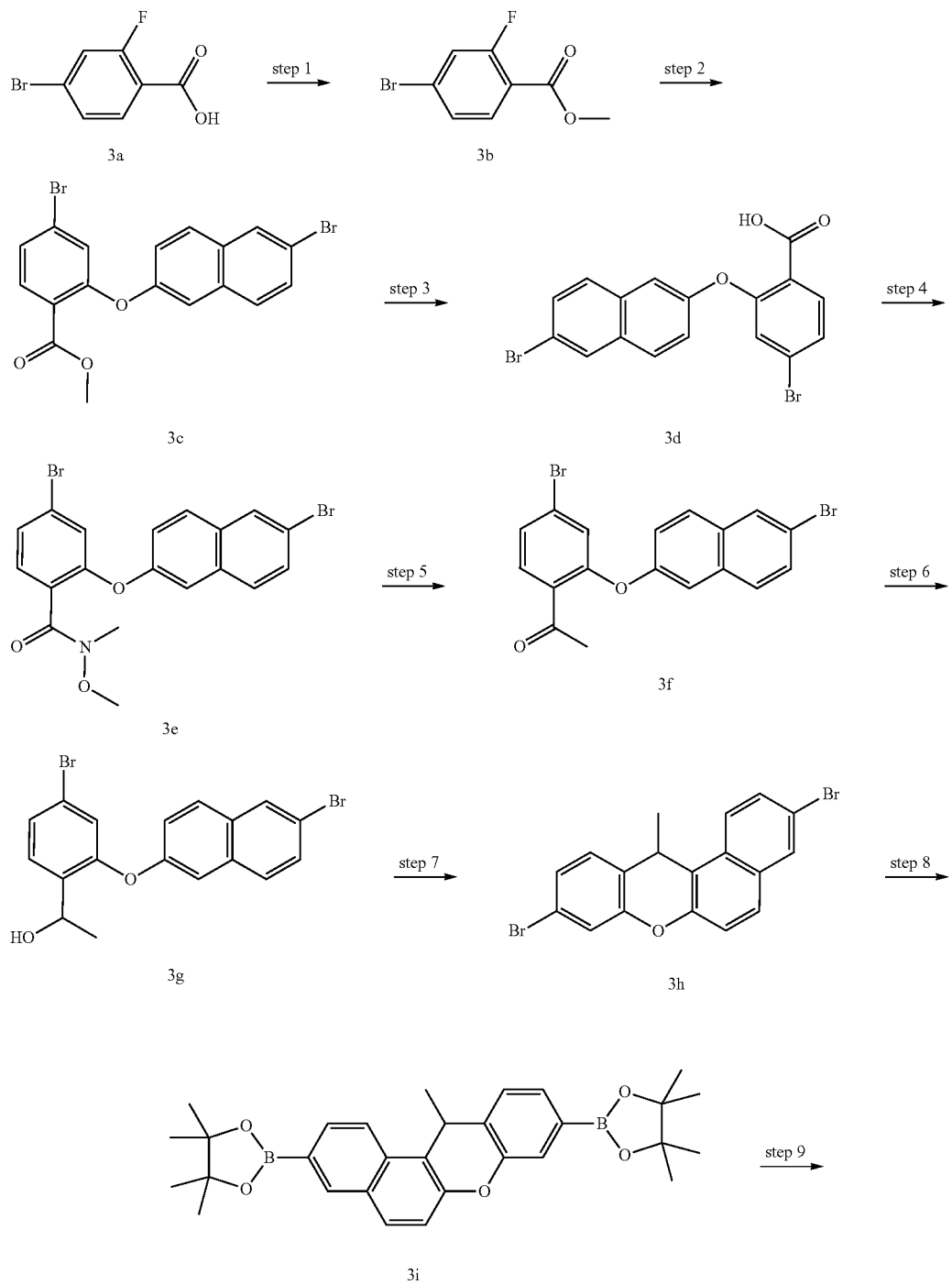

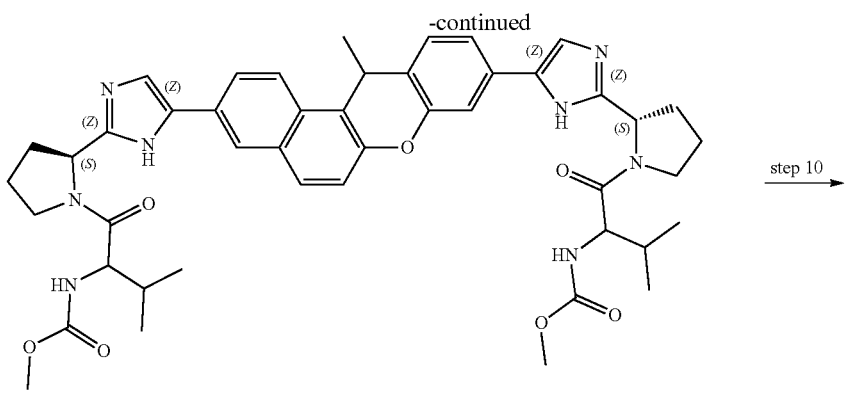

3j

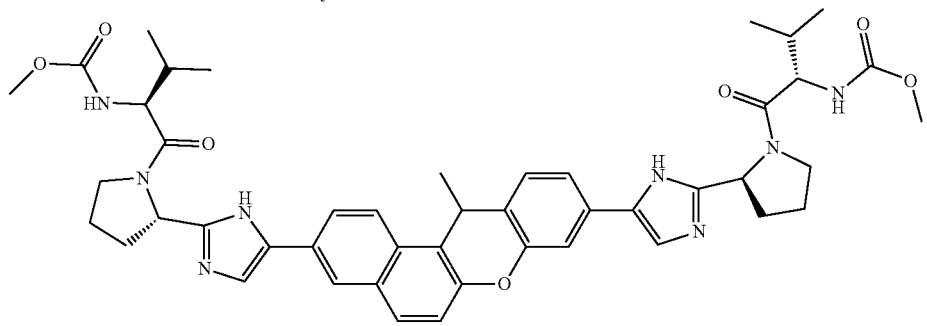

3

Step 1

To a solution of compound 3a (50 g, 210 mmol) in DCM (300 mL) was added oxalyl dichloride (40.38 g, 300 mmol) dropwise at room temperature. The reaction mixture was stirred at room temperature for 1 h. Then MeOH (50 ml) was added dropwise, the solution was stirred at room temperature for another 1 h. The solvent was removed to afford compound 3b (48 g, 93%).

Step 2

To a solution of 3b (52 g, 227 mmol) in DMF (1500 mL) was added $Cs_2CO_3$ (148 g, 454 mmol) and 6-bromonaphthalen-2-ol (45.8 g, 204 mmol). The reaction mixture was stirred at 100° C. for 12 h under $N_2$, before it was poured into water and extracted with EA. The combined organic phases were dried over $Na_2SO_4$. After filtration and concentration, the residue was purified by $SiO_2$ chromatography, eluting with petroleum ether:ethyl acetate (100/1~10/1) to afford compound 3c (65 g, 66.3%).

Step 3

To a solution of compound 3c (15 g, 34.5 mmol) in MeOH (20 mL) and $H_2O$ (20 mL) was added NaOH (6.9 g, 172.8 mmol). The mixture was stirred at 80° C. for 2h. After evaporation, the residue was re-dissolved into water and adjusted pH=6~7 with 3N HCl, then extracted with EA. The combined organic layers were washed with brine, dried over $Na_2SO_4$ and concentrated to afford compound 3d (13 g, 89%).

Step 4

To a solution of compound 3d (8 g, 19 mmol), N,O-dimethylhydroxylammonium chloride (2.43 g, 24.76 mmol) and $Et_3N$ (5.76 g, 57 mmol) in DMF (40 mL) was added HATU (7.22 g, 19 mmol) at 0° C. The mixture was stirred under $N_2$ at room temperature for 12 h before it was poured into water and extracted with DCM. The organic layer was washed with brine, dried over $Na_2SO_4$. After filtration and concentration, the residue was purified by $SiO_2$ chromatography, eluting with petroleum ether:ethyl acetate (10/1~1/1) to give compound 3e (8 g, 90.9%).

Step 5

To a solution of compound 3e (2.9 g, 6.26 mmol) in THF (30 mL) was added MeMgBr (3M solution in ether, 2.5 mL, 7.52 mmol) dropwise at 0° C. The mixture was stirred at 0° C. for 3 h before ice-water (50 mL) was added to quench the reaction, extracted with EA. The organic layer was washed with brine, dried over $Na_2SO_4$, filtered and concentrated to give 3f (2.3 g, 69%).

Step 6

To a solution of compound 3f (2.3 g, 5.45 mmol) in MeOH (30 mL) was added $NaBH_4$ (0.41 g, 10.9 mmol) at 0° C. The mixture was stirred under $N_2$ at 0° C. for 20 min, and then warmed to room temperature for 20 min. After filtration and concentration, the residue was portioned between water and EA. The organic layer was washed with brine, dried over $Na_2SO_4$, filtered and concentrated to give 3g (2 g, 86.6%).

Step 7

To a solution of compound 3g (530 mg, 1.25 mmol) in DCM (20 mL) was added $AlCl_3$ (333 mg, 2.5 mmol). The mixture was stirred under $N_2$ at room temperature for 30 min, before it was poured into water and extracted with DCM. The organic layer was washed with brine, dried over $Na_2SO_4$. After filtration and concentration, the residue was purified by $SiO_2$ chromatography, eluting with petroleum ether to give compound 3h (300 mg, 59.4%).

Step 8

The mixture of 3h (300 mg, 0.74 mmol), bis(pinacolato)diboron (415 mg, 1.63 mmol), KOAc (363 mg, 3.7 mmol) and Pd(dppf)Cl$_2$ (108 mg, 0.15 mmol) in dioxane (10 mL) was stirred at 100° C. for 2 hours under N$_2$ protection. The reaction mixture was cooled and concentrated in vacuum, and the residue was purified by SiO$_2$ chromatography, eluting with petroleum ether:ethyl acetate (20/1~5/1) to give 3i (300 mg, 81.5%).

Step 9

The mixture of 3i (300 mg, 0.6 mmol), Cap1 (493 mg, 1.325 mmol), Na$_2$CO$_3$ (318 mg, 3 mmol) and Pd(dppf)Cl$_2$ (66 mg, 0.09 mmol) in THF/H$_2$O/DMF (v/v=5/2/1, 16 mL) was stirred at 80° C. overnight under N$_2$ protection. After that, the mixture was washed with water and extracted with ethyl acetate, washed with brine and dried over anhydrous sodium sulfate. After filtrated, the filtrate was concentrated in vacuum, the residue was dissolved in DMF and purified by Pre-HPLC to give 3j (300 mg, 60.1%).

Step 10

Compound 3 was obtained from compound 3j (300 mg) by SFC separation by using the following conditions: Injection Volume: 5; Co-Solvent: IPA (0.05% DEA); Column: AS-H; Total Flow: 2.5; Wavelength: 340.

1H NMR (MeOD) δ 8.27-8.25 (d, J=8 Hz, 1H), 8.22 (s, 1H), 7.97-7.89 (m, 2H), 7.87-7.85 (d, J=8 Hz, 2H=), 7.58-7.56 (d, J=8 Hz, 1H), 7.21-7.23 (m, 2H), 7.39-7.37 (m, 1H), 5.28-5.22 (m, 2H), 4.25-4.22 (m, 2H), 4.10-4.09 (m, 2H), 3.93-3.87 (m, 2H), 3.65 (s, 6H), 2.57-2.54 (m, 2H), 2.29-2.23 (m, 2H), 2.17-2.13 (m, 4H), 2.10-2.05 (m, 2H), 1.51-1.49 (m, 3H), 0.99-0.86 (m, 13H). LC/MS: Anal. Calcd. For [M+H]$^+$ C$_{46}$H$_{54}$N$_8$O$_7$: 830.99; found 831.6.

Preparation of Compound 4

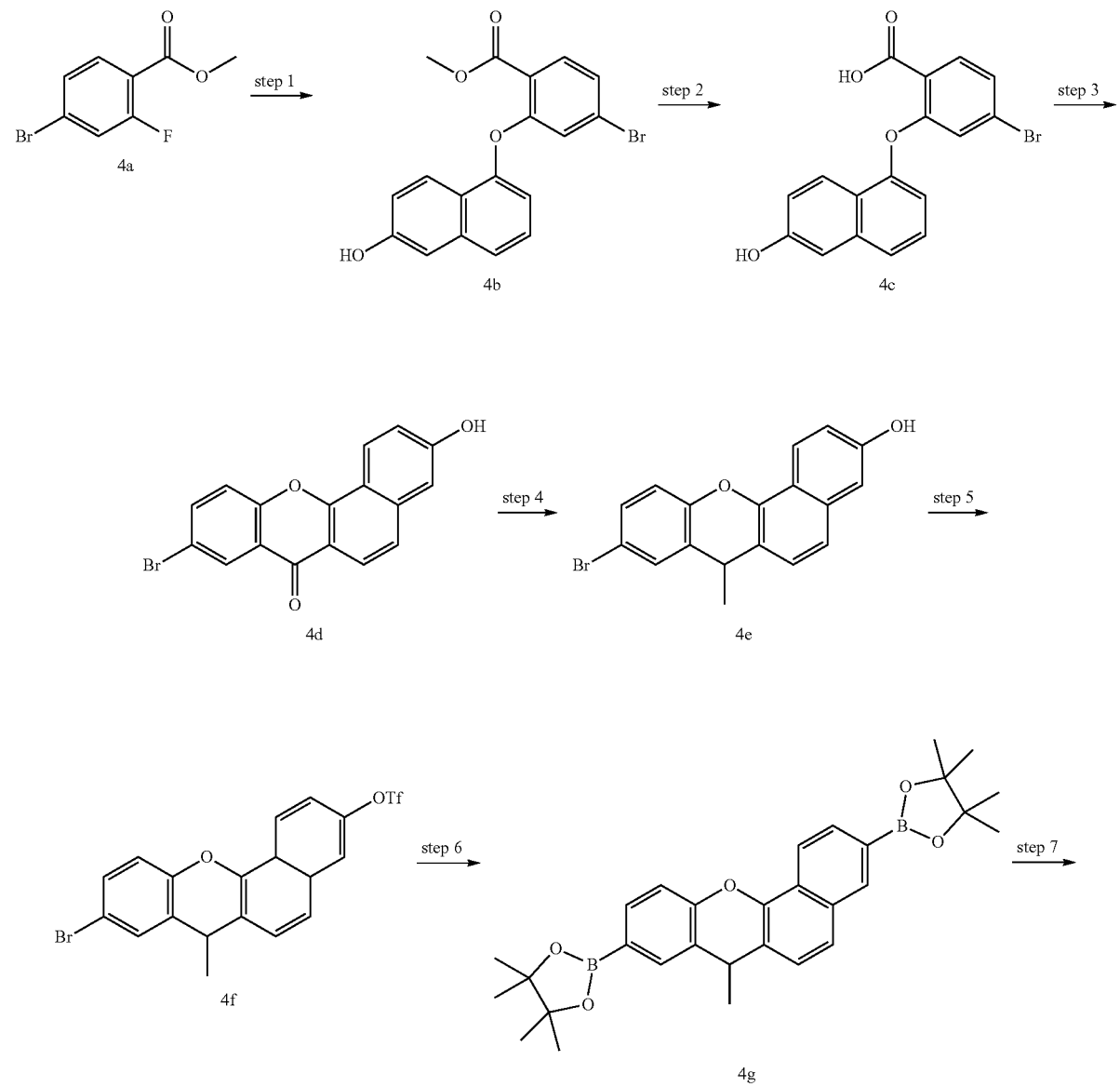

-continued

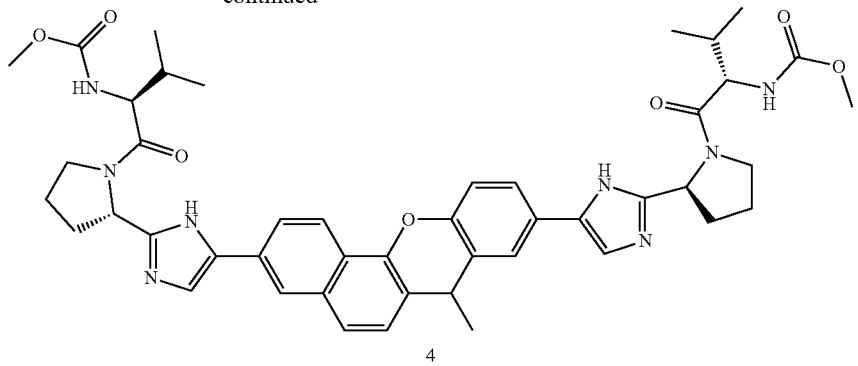

4

Step 1

To a solution of 4a (28 g, 113 mmol) in DMF (500 mL) was added naphthalene-1,6-diol (22 g, 136 mmol) and $Cs_2CO_3$ (74 g, 226 mmol). The resulting solution was stirred at 100° C. for 12 h, before it was poured into water and extracted with EA. The combined organic phases were dried over $Na_2SO_4$. After filtration and concentration, the residue was purified by $SiO_2$ chromatography, eluting with petroleum ether:ethyl acetate (100/1~10/1) to give compound 4b (25 g, 59.5%).

Step 2

To a solution of compound 4b (17.1 g, 45.8 mmol) in MeOH (60 mL) and $H_2O$ (20 mL) was added NaOH (9 g, 229 mmol). The mixture was stirred at 80° C. for 2 h before evaporated to remove the solvent. The residue was re-dissolved into water and adjusted pH=6~7 with 3N HCl, and then extracted with EA (30 ml). The combined organic layers were washed with brine, dried over $Na_2SO_4$ and concentrated to afford compound 4c (13 g, 79%).

Step 3

To a solution of compound 4c (5.91 g, 16.4 mmol) in DCM (60 mL) was added TFAA (4.13 g, 19.7 mmol) and $BF_3.OEt_2$ (233 mg, 1.64 mmol). The mixture was stirred under $N_2$ at room temperature for 12 h, before it was poured into water and extracted with DCM. The organic layer was washed with brine, dried over sodium sulfate. After filtration and concentration, the residue was purified by $SiO_2$ chromatography, eluting with petroleum ether to give compound 4d (3.6 g, 64.3%).

Step 4

To a solution of compound 4d (100 mg, 0.29 mmol) in THF (10 mL) was added MeMgBr (3M solution in ether, 2.5 mL, 7.52 mmol) dropwise at 0° C. The mixture was stirred at 0° C. for 2 h before ice-water (10 mL) was added to quench the reaction, extracted with EA. The organic layer was washed with brine, dried over sodium sulfate, filtered and concentrated. The residue was dissolved in 10 ml of DCM, and then to the mixture was added $HSiEt_3$ (490 mg, 4.22 mmol) and TFA (319 mg, 2.8 mmol) at 0° C. The mixture was stirred at 0° C. for 12 h before ice-water (20 mL) was added to quench the reaction, extracted with EA. The organic layer was washed with brine, dried over sodium sulfate, filtered and concentrated to give 4e (70 mg, 69.5%).

Step 5

To a solution of compound 4e (70 mg, 0.21 mmol) and pyridine (34 mg, 0.42 mmol) in DCM (20 mL) was added $Tf_2O$ (87 mg, 0.31 mmol) at 0° C. The mixture was stirred under $N_2$ at room temperature for 30 min before it was poured into water and extracted with DCM. The organic layer was washed with brine, dried over sodium sulfate. After filtration and concentration, the residue was purified by $SiO_2$ chromatography, eluting with petroleum ether to give compound 4f (50 mg, 63.5%).

Step 6

The mixture of 4f (50 mg, 0.134 mmol), bis(pinacolato)diboron (75 mg, 0.294 mmol), KOAc (66 mg, 0.67 mmol) and $Pd(dppf)Cl_2$ (20 mg, 0.027 mmol) in dioxane (10 mL) was stirred at 100° C. for 2 hours under $N_2$ protection. The reaction mixture was cooled and concentrated in vacuum, and the residue was purified by $SiO_2$ chromatography, eluting with petroleum ether:ethyl acetate (20/1~5/1) to give 4g (50 mg, 74.9%).

Step 7

The mixture of 4g (50 mg, 0.1 mmol), Cap1 (82 mg, 0.22 mmol), $Na_2CO_3$ (53 mg, 0.5 mmol) and $Pd(dppf)Cl_2$ (11 mg, 0.015 mmol) in $THF/H_2O/DMF$ (v/v=5/2/1, 3 mL) was stirred at 80° C. overnight under $N_2$ protection. After that, the mixture was washed with water and extracted with ethyl acetate, washed with brine and dried over anhydrous sodium sulfate. After filtrated, the filtrate was concentrated in vacuum, the residue was dissolved in DMF and purified by Pre-HPLC to give 4. $^1$H NMR (MeOD) δ: 8.43 (s, 1H), 8.20 (s, 1H), 7.93 (s, 1H), 7.84-7.71 (m, 3H), 7.58-7.52 (m, 2H), 7.50-7.44 (m, 1H), 7.37 (s, 1H), 5.24-5.22 (m, 2H), 4.31 (s, 1H), 4.22-4.08 (m, 2H), 3.88 (s, 2H), 3.63-3.57 (m, 2H), 3.42 (s, 6H), 3.28 (s, 5H), 2.57-2.51 (m, 2H), 2.27-1.99 (m, 4H), 1.56 (s, 2H), 0.92-0.87 (m, 12H). LC/MS: Anal. Calcd. For $[M+H]^+$ $C_{46}H_{54}N_8O_7$: 830.99; found 831.2.

Preparation of Compound 7

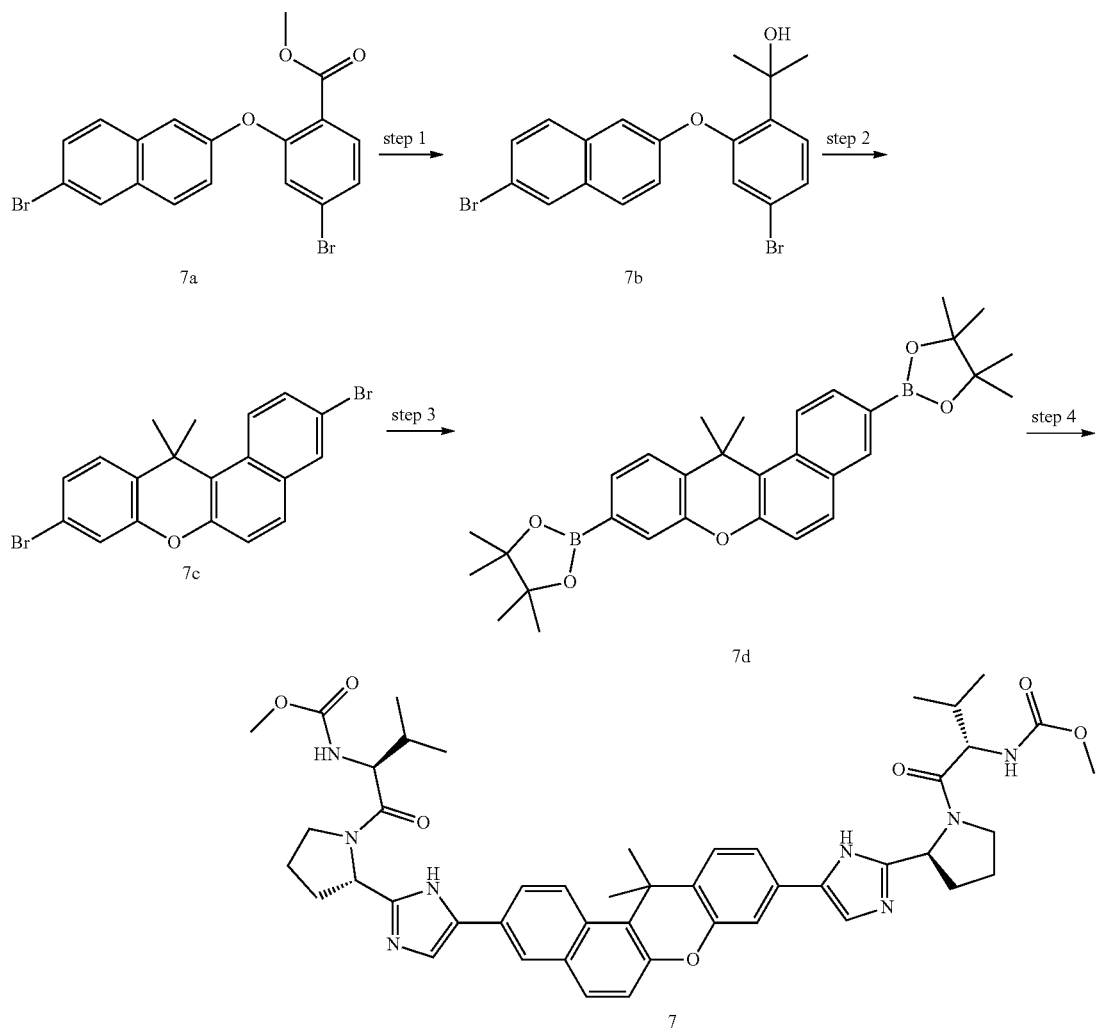

Step 1

Preparation of compound 7a was described in the preparation of Compound 3. To a solution of compound 7a (500 mg, 1.15 mmol) in THF (20 mL) was added MeMgBr (3M solution in aether, 1 mL, 2.88 mmol) dropwise at 0° C. The mixture was stirred at 0° C. for 3 h before ice-water (50 mL) was added to quench the reaction, extracted with EA. The organic layer was washed with brine, dried over $Na_2SO_4$. After filtration and concentration, the residue was purified by $SiO_2$ chromatography, eluting with petroleum ether:ethyl acetate (20/1~4/1) to give compound 7b (400 mg, 80%).

Step 2

To a solution of compound 7b (400 mg, 0.92 mmol) in DCM (20 mL) was added $AlCl_3$ (247 mg, 1.84 mmol). The mixture was stirred under $N_2$ at room temperature for 30 min, before it was poured into water and extracted with DCM. The organic layer was washed with brine, dried over $Na_2SO_4$. After filtration and concentration, the residue was purified by $SiO_2$ chromatography, eluting with petroleum ether to give compound 7c (300 mg, 78%).

Step 3

The mixture of 7c (416 mg, 1 mmol), (559 mg, 2.2 mmol), KOAc (490 mg, 5 mmol) and $Pd(dppf)Cl_2$ (146 mg, 0.2 mmol) in dioxane (15 mL) was stirred at 100° C. for 2 hours under $N_2$ protection. The reaction mixture was cooled and concentrated in vacuum, and the residue was purified by $SiO_2$ chromatography, eluting with petroleum ether:ethyl acetate (20/1~5/1) to give 7d (450 mg, 87.9%).

Step 4

The mixture of 7d (225 mg, 0.44 mmol), Cap1 (358 mg, 0.96 mmol), $Na_2CO_3$ (233 mg, 2.2 mmol) and $Pd(dppf)Cl_2$ (50 mg, 0.066 mmol) in $THF/H_2O/DMF$ (v/v=5/2/1, 16 mL) was stirred at 80° C. overnight under $N_2$ protection. After that, the mixture was washed with water and extracted with ethyl acetate, washed with brine and dried over anhydrous sodium sulfate. After filtrated, the filtrate was concentrated in vacuum, the residue was dissolved in DMF and purified by Pre-HPLC to give 7. $^1H$ NMR (MeOD) δ: 8.52-8.50 (d, J=8 Hz, 1H), 8.13 (s, 1H), 7.87-7.83 (m, 1H), 7.76-7.74 (m, 1H), 7.64-7.62 (d, J=8 Hz, 2H), 7.44-7.42 (d, J=8 Hz, 2H), 7.24 (s, 1H), 7.18-7.16 (d, J=8 Hz, 1H), 5.30-5.23 (m, 2H), 4.28-4.10 (m, 4H), 3.96-3.92 (m, 2H), 3.65 (s, 6H), 2.57-2.55 (m, 3H), 2.29-2.22 (m, 3H), 2.19-2.09 (m, 5H), 2.03 (s, 6H), 0.98-0.89 (m, 12H). LC/MS: Anal. Calcd. For $[M+H]^+$ $C_{47}H_{56}N_8O_7$: 845.02; found 845.6.

Preparation of Compound 11

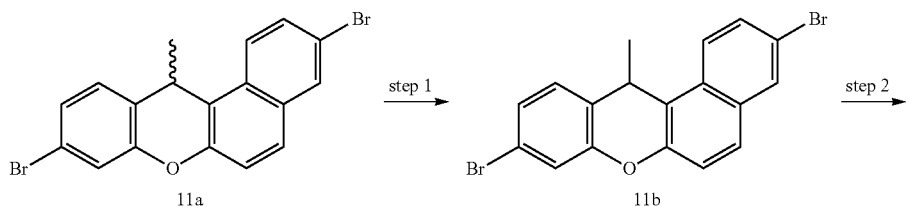

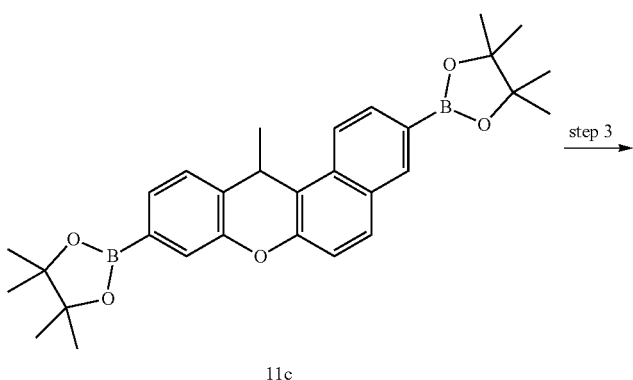

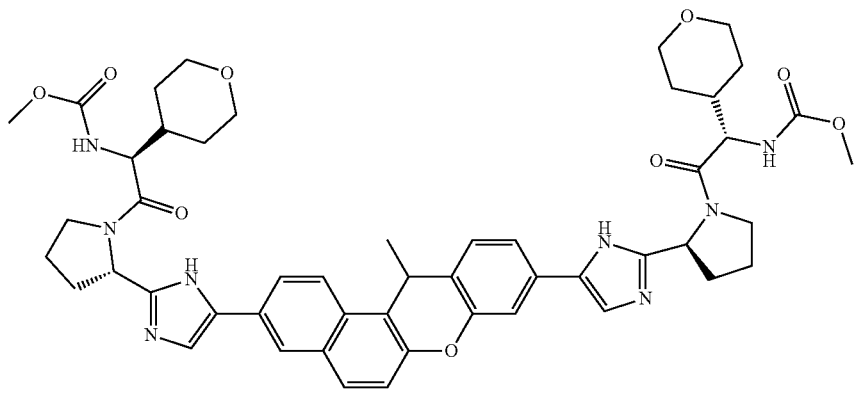

Step 1

Preparation of compound 11a was described in the preparation of Compound 3. Compound 11b (400 mg) was obtained from compound 11a (1 g) by SFC separation by using the following conditions: Injection Volume: 3; Co-Solvent: IPA (0.05% DEA); Column: OJ-3; Total Flow: 2.5; Wavelength: 220.

Step 2

The mixture of compound 11b (404 mg, 1 mmol), bis(pinacolato)diboron (559 mg, 2.2 mmol), KOAc (490 mg, 5 mmol) and Pd(dppf)Cl$_2$ (146 mg, 0.2 mmol) in dioxane (15 mL) was stirred at 100° C. for 2 hours under N$_2$ protection. The reaction mixture was cooled and concentrated in vacuum, and the residue was purified by SiO$_2$ chromatography, eluting with petroleum ether:ethyl acetate (20/1~5/1) to give compound 11c (450 mg, 90.3%).

Step 3

A suspension of 11c (297 mg, 0.6 mmol), Cap2 (50 mg, 0.12 mmol), Na$_2$CO$_3$ (318 mg, 3 mmol) and Pd(dppf)Cl$_2$ (66 mg, 0.09 mmol) in THF/H$_2$O/DMF (v/v=5/2/1, 16 mL) was stirred at 80° C. overnight under N$_2$ protection. After that, the mixture was washed with water and extracted with ethyl acetate, washed with brine and dried over anhydrous sodium sulfate. After filtrated, the filtrate was concentrated in vacuum, the residue was dissolved in DMF and purified by Pre-HPLC to give 11. $^1$H NMR (MeOD) δ: 8.15 (s, 1H), 7.91-7.87 (m, 2H), 7.67-7.64 (m, 1H), 7.56-7.49 (m, 3H), 7.20-7.17 (m, 1H), 7.10 (s, 1H), 5.29-5.22 (m, 2H), 4.57 (s, 1H), 4.39-4.33 (m, 2H), 4.17-4.13 (m, 4H), 4.03-3.90 (m, 5H), 3.68 (s, 6H), 3.45-3.30 (m, 5H), 2.57-2.56 (m, 2H), 2.32-2.29 (m, 4H), 1.62-1.33 (m, 12H). LC/MS: Anal. Calcd. For [M+H]$^+$ C$_{50}$H$_{58}$N$_8$O$_9$: 915.06; found 915.6.

Preparation of Compound 13

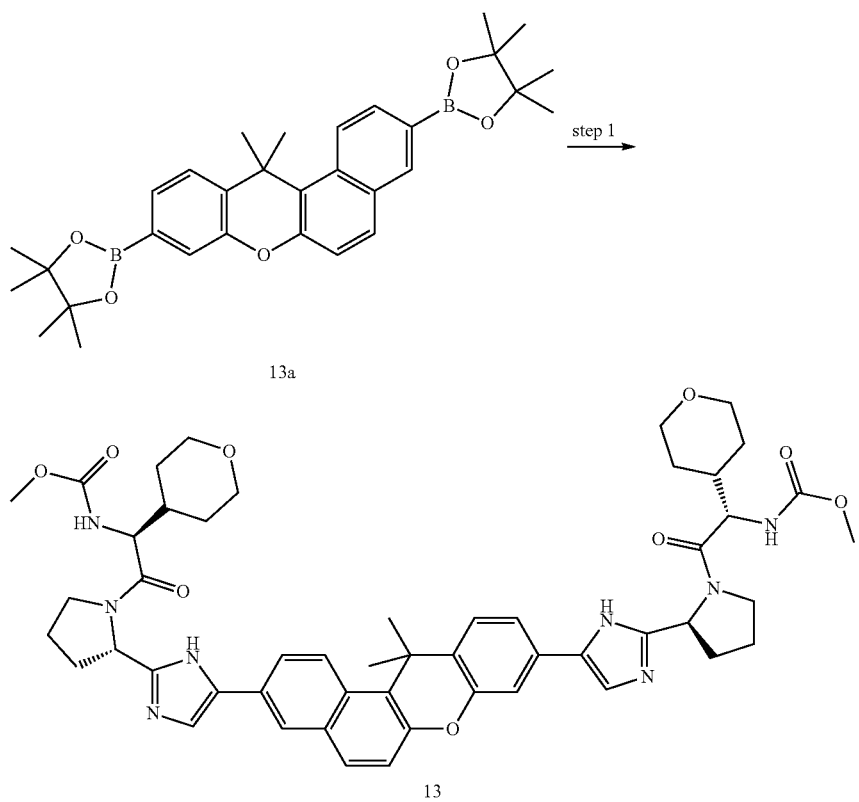

Step 1

Preparation of compound 13a was described in the preparation of Compound 7. The mixture of 13a (225 mg, 0.44 mmol), Cap2 (401 mg, 0.96 mmol), Na$_2$CO$_3$ (233 mg, 2.2 mmol) and Pd(dppf)Cl$_2$ (50 mg, 0.066 mmol) in THF/H$_2$O/DMF (v/v=5/2/1, 16 mL) was stirred at 80° C. overnight under N$_2$ protection. After that, the mixture was washed with water and extracted with ethyl acetate, washed with brine and dried over anhydrous sodium sulfate. After filtrated, the filtrate was concentrated in vacuum, the residue was dissolved in DMF and purified by Pre-HPLC to give 13. $^1$H NMR (MeOD) δ: 8.54-8.52 (d, 1H, J=8 Hz), 8.16 (s, 1H), 7.88-7.82 (m, 2H), 7.78-7.76 (m, 2H), 7.65-7.63 (d, J=8 Hz, 1H), 7.44-7.42 (d, J=8 Hz, 1H), 7.20-7.18 (m, 2H), 5.29-5.23 (m, 2H), 3.46-3.29 (m, 5H), 3.98-3.89 (m, 5H), 3.65 (s, 6H), 3.46-3.29 (m, 5H), 2.56-2.54 (m, 2H), 2.28-2.05 (m, 10H), 1.99-1.39 (m, 10H). LC/MS: Anal. Calcd. For [M+H]$^+$ C$_{51}$H$_{60}$N$_8$O$_9$: 929.09; found 929.6.

Using the appropriate intermediates and procedures outlined above, the following compounds were prepared.

| Compound | structure | Isomer | Observed MWt | [M + 1]+ |
|---|---|---|---|---|
| 1 | 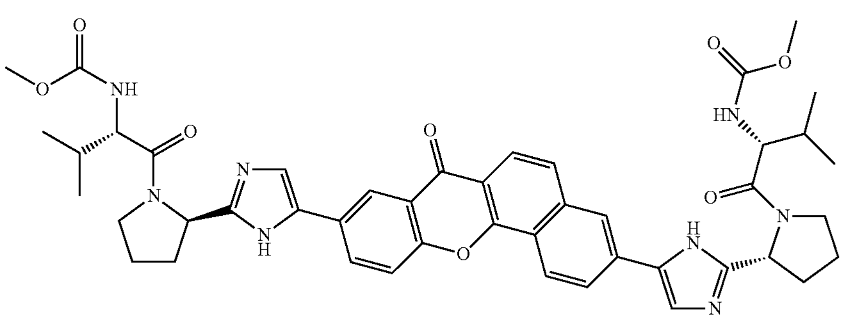 [SMILES: COC(=O)N[C@H](C(=O)N1CCC[C@@H]1c1ncc(-c2ccc3oc4c(ccc5cc(-c6cnc([C@H]7CCCN7C(=O)[C@H](NC(=O)OC)C(C)C)[nH]6)ccc54)c(=O)c3c2)[nH]1)C(C)C] | | 830.949 | 831.4 |

-continued

| Compound | structure | Isomer | MWt | Observed [M + 1]+ |
|---|---|---|---|---|
| 2 | 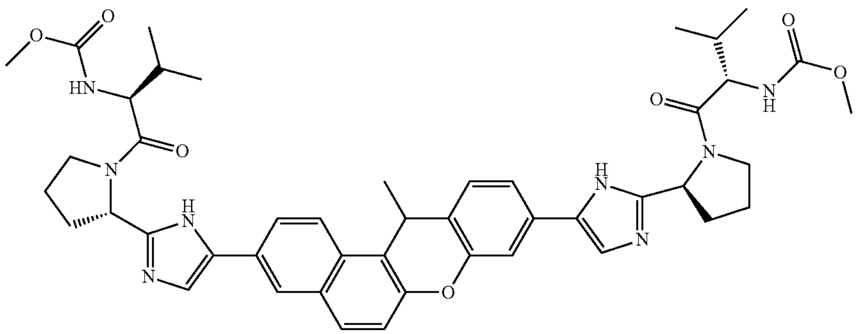 | Isomer 2 | 830.993 | 831.4 |
| 3 | | Isomer 1 | 830.993 | 831.6 |
| 4 | 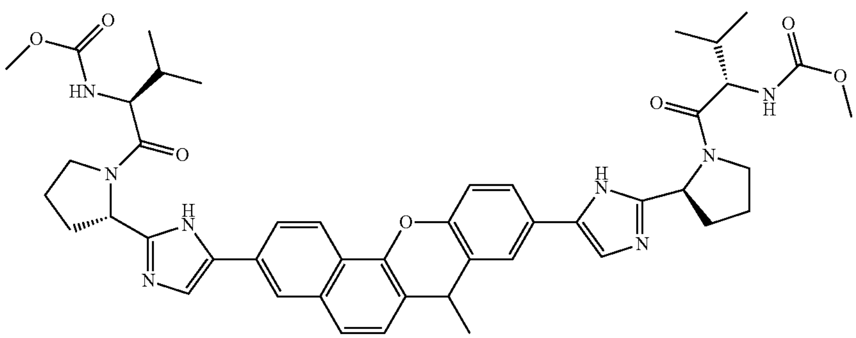 | | 830.993 | 831.2 |
| 5 | 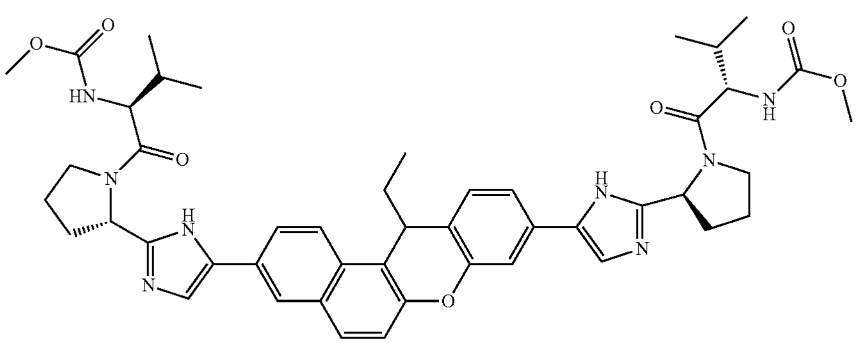 | Isomer 1 | 845.02 | 845.6 |
| 6 | | Isomer 2 | 845.02 | 845.2 |
| 7 | 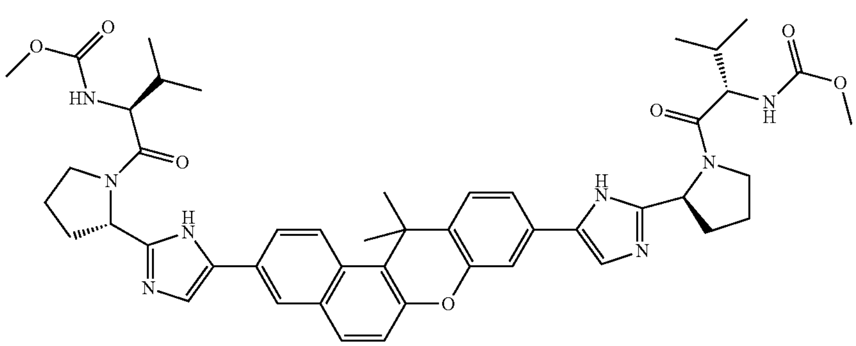 | | 845.02 | 845.6 |

| Compound | structure | Isomer | MWt | Observed [M + 1]+ |
|---|---|---|---|---|
| 8 | 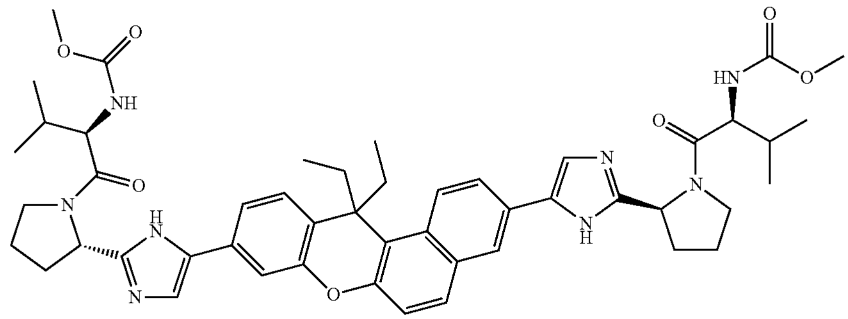 [SMILES: CCC1(CC)c2ccc(-c3cnc([C@@H]4CCCN4C(=O)[C@H](NC(=O)OC)C(C)C)[nH]3)cc2Oc2ccc3cc(-c4cnc([C@@H]5CCCN5C(=O)[C@@H](NC(=O)OC)C(C)C)[nH]4)ccc3c21] | | 873.074 | 873.4 |
| 9 | 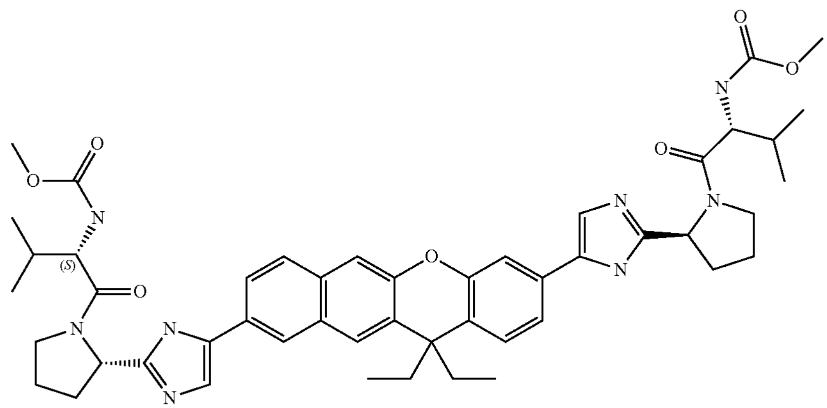 | | 873.074 | 873.4 |
| 10 | blank | | | |
| 11 | 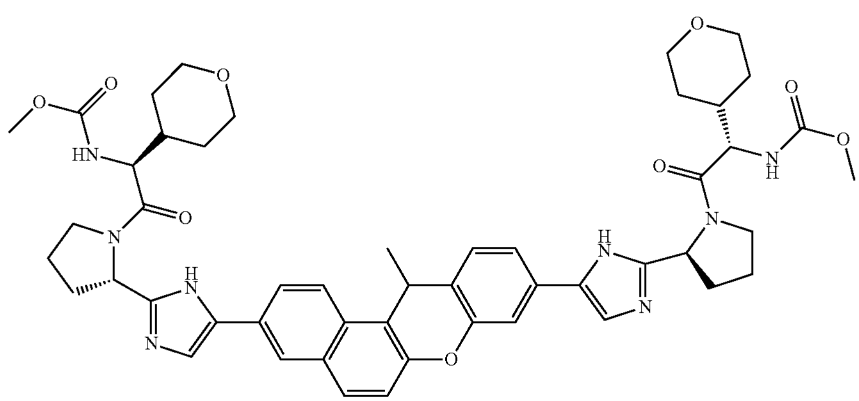 | Isomer 1 | 915.068 | 915.6 |
| 12 | | Isomer 2 | 915.068 | 915.4 |
| 13 | 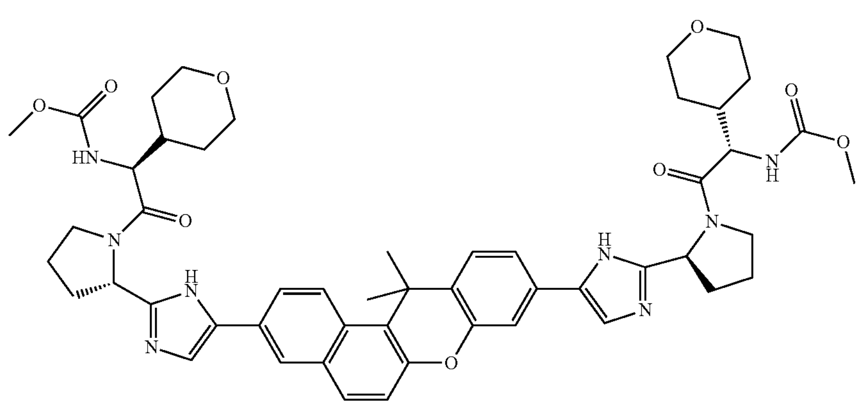 | | 929.095 | 929.6 |

-continued

| Compound | structure | Isomer | MWt | Observed [M + 1]+ |
|---|---|---|---|---|
| 14 | 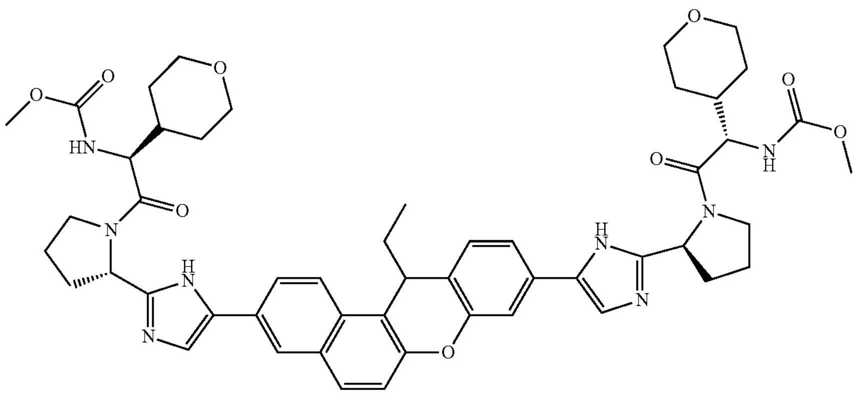 | Isomer 1 | 929.095 | 929.4 |
| 15 | | Isomer 2 | 929.095 | 929.6 |
| 16 | 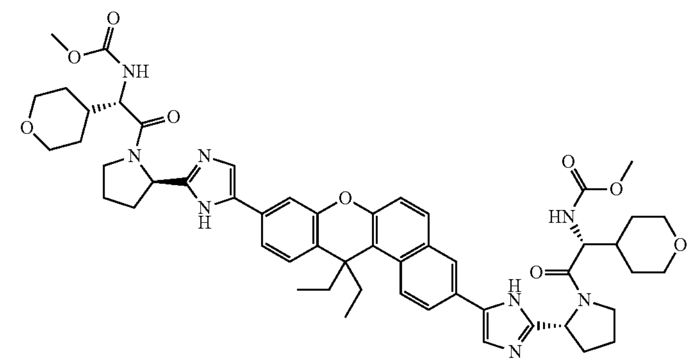 [SMILES: CCC1(CC)c2ccc(-c3cnc([C@H]4CCCN4C(=O)[C@@H](NC(=O)OC)C4CCOCC4)[nH]3)cc2Oc2ccc3cc(-c4cnc([C@H]5CCCN5C(=O)[C@H](NC(=O)OC)C5CCOCC5)[nH]4)ccc3c21] | | 957.149 | 957.4 |
| 17 | 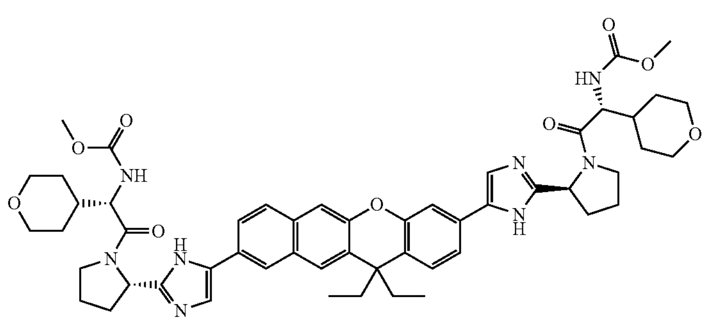 [SMILES: CCC1(CC)c2ccc(-c3cnc([C@@H]4CCCN4C(=O)[C@H](NC(=O)OC)C4CCOCC4)[nH]3)cc2Oc2cc3ccc(-c4cnc([C@@H]5CCCN5C(=O)[C@@H](NC(=O)OC)C5CCOCC5)[nH]4)cc3cc21] | | 957.149 | 957.4 |
| 18 | 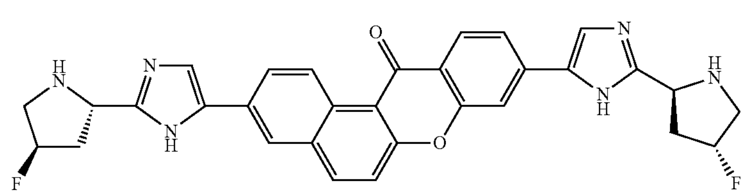 [SMILES: O=c1c2ccc(-c3cnc([C@@H]4C[C@@H](F)CN4)[nH]3)cc2oc2ccc3cc(-c4cnc([C@@H]5C[C@@H](F)CN5)[nH]4)ccc3c12] | | 552.589 | 553.2 |
| 19 | 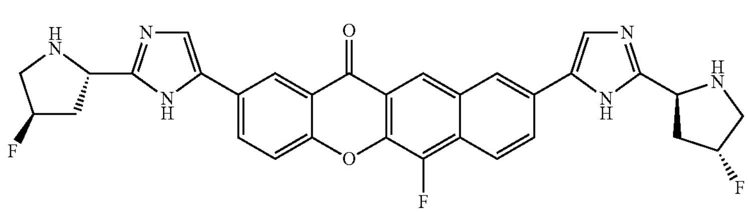 [SMILES: O=c1c2cc(-c3cnc([C@@H]4C[C@@H](F)CN4)[nH]3)ccc2oc2c(F)c3ccc(-c4cnc([C@@H]5C[C@@H](F)CN5)[nH]4)cc3cc12] | | 570.579 | 571.3 |

-continued

| Compound | structure | Isomer | MWt | Observed [M + 1]+ |
|---|---|---|---|---|
| 20 | 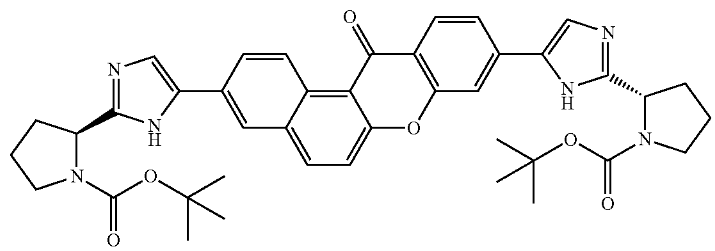 [SMILES: CC(C)(C)OC(=O)N1CCC[C@H]1c1ncc(-c2ccc3c(ccc4oc5cc(-c6cnc([C@@H]7CCCN7C(=O)OC(C)(C)C)[nH]6)ccc5c(=O)c43)c2)[nH]1] | | 716.844 | 717.4 |
| 21 | 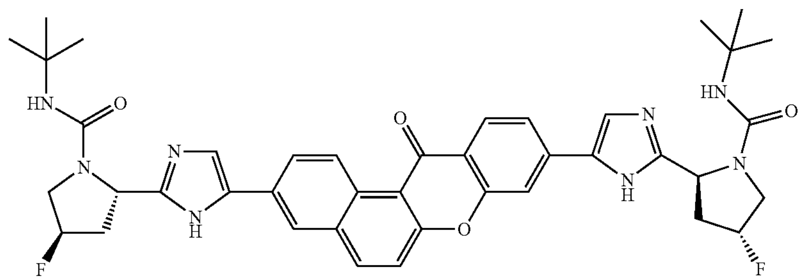 [SMILES: CC(C)(C)NC(=O)N1C[C@H](F)C[C@H]1c1ncc(-c2ccc3c(ccc4oc5cc(-c6cnc([C@@H]7C[C@@H](F)CN7C(=O)NC(C)(C)C)[nH]6)ccc5c(=O)c43)c2)[nH]1] | | 750.856 | 751.4 |
| 22 | 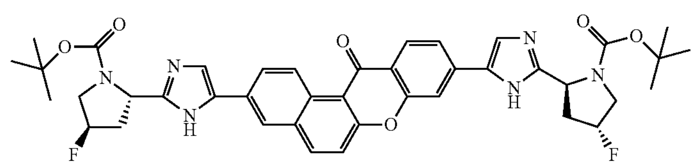 [SMILES: CC(C)(C)OC(=O)N1C[C@H](F)C[C@H]1c1ncc(-c2ccc3c(ccc4oc5cc(-c6cnc([C@@H]7C[C@@H](F)CN7C(=O)OC(C)(C)C)[nH]6)ccc5c(=O)c43)c2)[nH]1] | | 752.825 | 753.4 |
| 23 | 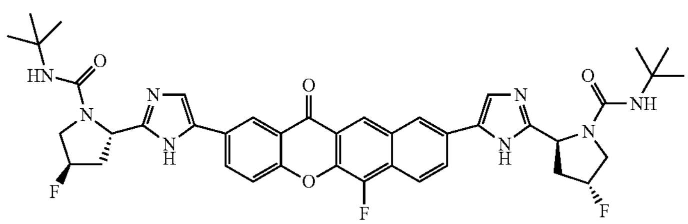 [SMILES: CC(C)(C)NC(=O)N1C[C@H](F)C[C@H]1c1ncc(-c2ccc3c(F)c4oc5ccc(-c6cnc([C@@H]7C[C@@H](F)CN7C(=O)NC(C)(C)C)[nH]6)cc5c(=O)c4cc3c2)[nH]1] | | 768.846 | 769.4 |
| 24 | 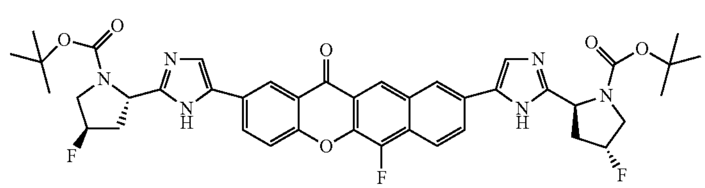 [SMILES: CC(C)(C)OC(=O)N1C[C@H](F)C[C@H]1c1ncc(-c2ccc3c(F)c4oc5ccc(-c6cnc([C@@H]7C[C@@H](F)CN7C(=O)OC(C)(C)C)[nH]6)cc5c(=O)c4cc3c2)[nH]1] | | 770.816 | 771.3 |
| 25 | 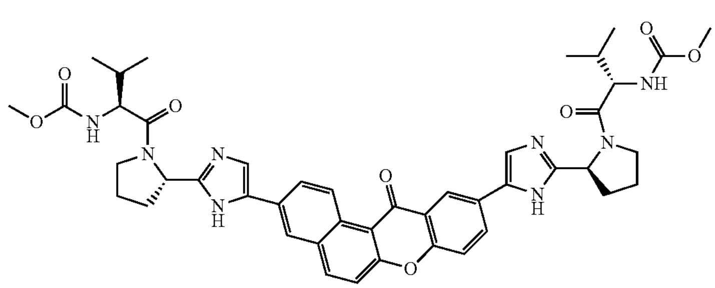 | | 830.949 | 831.5 |

-continued

| Compound | structure | Isomer | MWt | Observed [M + 1]+ |
|---|---|---|---|---|
| 26 | 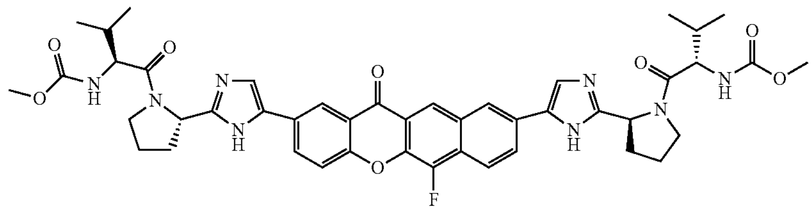 | | 848.939 | 849.4 |
| 27 | 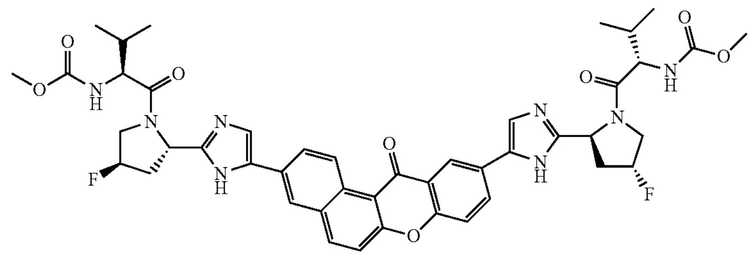 | | 866.93 | 867.5 |
| 28 | 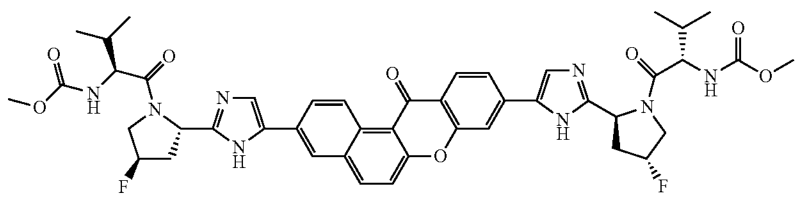 | | 866.93 | 867.3 |
| 29 | 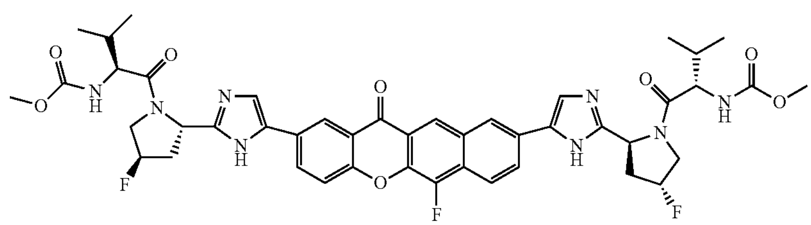 | | 884.92 | 885.4 |
| 30 | 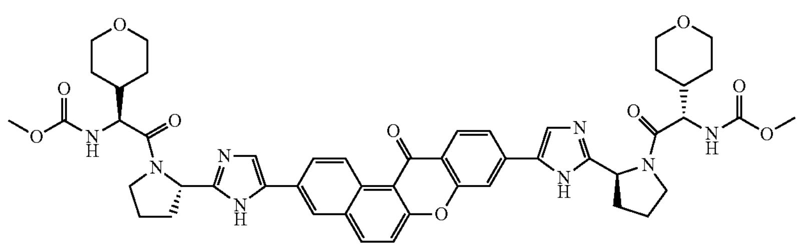 | | 915.024 | 915.4 |
| 31 | 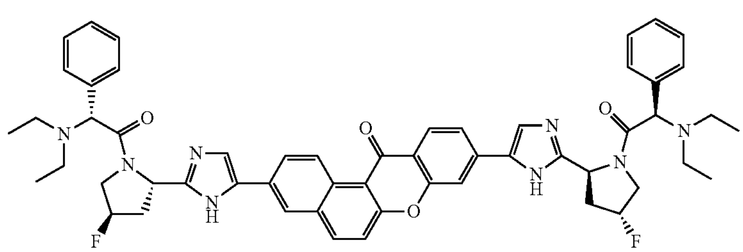 [SMILES: CCN(CC)[C@@H](C(=O)N1C[C@H](F)C[C@H]1c1ncc(-c2ccc3c(ccc4oc5cc(-c6cnc([C@@H]7C[C@@H](F)CN7C(=O)[C@@H](c7ccccc7)N(CC)CC)[nH]6)ccc5c(=O)c43)c2)[nH]1)c1ccccc1] | | 931.108 | 931.4 |

| Compound | structure | Isomer | MWt | Observed [M + 1]+ |
|---|---|---|---|---|
| 32 | 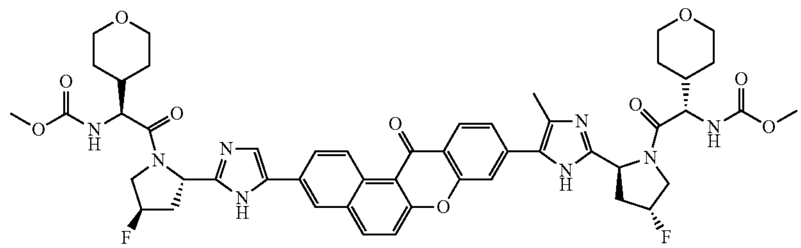 | | 951.005 | 951.4 |
| 33 | 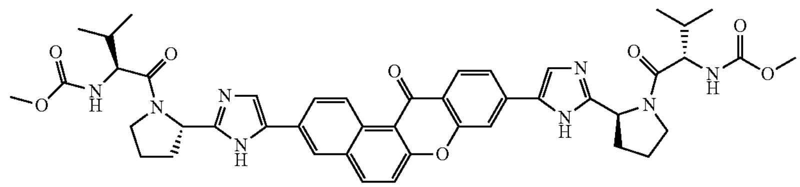 | | 830.949 | 831.5 |

Assays

HCV Replicon Assay

General procedure: Huh-7 cells containing HCV Con1 subgenomic replicon (GS4.1 cells) were grown in Dulbecco's Modified Eagle Medium (DMEM) supplemented with 10% fetal bovine serum (FBS), 2 mM L-glutamine, 110 mg/L sodium pyruvate, 1× non-essential amino acids, 100 U/mL penicillin-streptomycin, and 0.5 mg/mL G418 (Invitrogen). For dose-response testing, the cells were seeded in 96-well plates at $7.5 \times 10^3$ cells/well in a volume of 50 µL, and incubated at 37° C./5% $CO_2$. Three hours after plating, 50 µL of ten 2-fold serial dilutions of compounds (highest concentration, 75 µM) were added, and cell cultures were incubated at 37° C./5% $CO_2$ in the presence of 0.5% DMSO. Alternatively, compounds were tested at a single concentration of 15 µM. In all cases, Huh-7 cells lacking the HCV replicon served as negative control. The cells were incubated in the presence of compounds for 72 hrs after which they were monitored for expression of the NS5A protein by enzyme-linked immunosorbent assay (ELISA). For this, the plates were then fixed for 1 min with acetone/methanol (1:1, v/v), washed twice with phosphate-buffered saline (PBS), 0.1% Tween 20, blocked for 1 hr at room temperature with TNE buffer containing 10% FBS and then incubated for 2 hr at 37° C. with the anti-NS5A mouse monoclonal antibody A-236 (ViroGen) diluted in the same buffer. After washing three times with PBS, 0.1% Tween 20, the cells were incubated 1 hr at 37° C. with anti-mouse immunoglobulin G-peroxidase conjugate in TNE, 10% FBS. After washing as described above, the reaction was developed with O-phenylenediamine (Zymed). The reaction was stopped after 30 min with 2 N $H_2SO_4$, and absorbance was read at 492 nm using Sunrise Tecan spectrophotometer. $EC_{50}$ values were determined from the % inhibition versus concentration data using a sigmoidal non-linear regression analysis based on four parameters with Tecan Magellan software. When screening at a single concentration, the results were expressed as % inhibition at 15 µM.

For cytotoxicity evaluation, GS4.1 cells were treated with compounds as described above and cellular viability was monitored using the Cell Titer 96 $AQ_{ueous}$ One Solution Cell Proliferation Assay (Promega). $CC_{50}$ values were determined from the % cytotoxicity versus concentration data with Tecan Magellan software as described above.

Generation of HCV NS5A-intergenotypic Stable Cell Lines for Genotypes 1a, 2a, 3a, and 4a The nucleotide sequences of the NS5A region of genotype 2a (GenBank Accession # AB047639), genotype 3a (GenBank Accession # D17763), and genotype 4a (GenBank Accession # DQ418788) were synthesized by an outside vendor. The NS5A region of each of these genotypes included the first 11 amino acids of the protease recognition sequence of genotype 1b, as well as the last 10 amino acids of genotype 1b. The NS5A gene cassettes were excised with site specific restriction endonucleases and ligated into a ZS11-luciferase genotype 1b backbone (backbone contains the genotype 1b NS3 protease, NS4a, NS4b, and NS5b coding regions) with similarly cut restriction enzyme sites. Thus, the newly constructed plasmid contains a genotype 2a-, 3a- or 4a-specific NS5A gene within the 1b-replicon.

To generate the 1a-H77 NS5a intergenotypic plasmid, dual cut sites were inserted into the ZS11-lucifrease genotype 1b backbone that would bracket the NS5a region almost in its entirety. Using PCR and 1a-H77 specific primers also containing the corresponding restriction enzyme sites, the NS5a gene was amplified from the 1a-H77 replicon. The ZS11-luciferase genotype 1b backbone and the genotype 1a NS5A PCR products were restriction enzyme digested and then ligated using standard molecular cloning techniques. The newly constructed plasmid contains the genotype 1a-specific NS5a gene where as the backbone remains 1b as described herein.

These new intergenotypic plasmids were used to establish stable cell lines. RNA was generated from the NS5A intergenotypic plasmids and used in conjunction with a lipofectin reagent to transfect a cured Huh7 cell line. Transfected cells were selected for with G418. After selection has occurred the stable cell lines were propagated, tested for luciferase activity, and RT-PCR with genotype specific primers (either 1a, 2a, 3a, or 4a). Stable cell lines containing the intergenotypic replicon were then fully sequenced and analyzed for proper expression of NS3, NS5A and NS5B proteins.

Drug titration analysis was performed using the luciferase replicon assay described herein.

Genotype 2a Infectious Virus Assay

The genotype 2a infectious virus assay measures the ability of a test compound to inhibit HCV replication in cell culture after 5 days of treatment at the time of HCV genotype 2a virus infection of a permissive human hepatoma cell line (HPC cells). The inhibition of HCV replication was measured by quantification of HCV core protein expression by an enzyme-linked immunosorbent assay (ELISA). Briefly, HPC cells were grown in DMEM containing glucose, L-glutamine and sodium pyruvate, 10% FBS, 100 IU/mL penicillin, 100 µg/mL streptomycin, 2 mM GlutaMAX, and non-essential amino acids. GlutaMAX was obtained from Invitrogen, Corp.; all other media reagents were obtained from Mediatech, Inc. For dose-response testing, ninety-six-well plates were seeded with HPC cells at a density of $2.5\times10^3$ cells/well in a volume of 50 µL, and incubated at 37° C./5% $CO_2$. Three hours after plating, 50 µL of ten 5-fold serial dilutions of compound and 100 µL of genotype 2a virus were added, and cell cultures were incubated at 37° C./5% $CO_2$. In all cases, mock infected HPC cells served as negative control. At 16 hours post treatment and infection, the virus inoculum was removed by aspiration. The cultures were treated at the same final concentrations of drug diluted in media and incubated for 4 additional days at 37° C./5% $CO_2$. Subsequently, the core ELISA was performed as follows. The plates were fixed for 90 seconds with acetone/methanol (1:1, v/v), washed three times with KPL wash solution (KPL, Inc.), blocked for 1 hr at room temperature with TNE buffer containing 10% FBS and then incubated for 2 hr at 37° C. with the anti-HCV core mouse monoclonal antibody (Thermo Scientific) diluted in the same buffer. After washing three times with KPL wash solution, the cells were incubated for 1 hr at 37° C. with an anti-mouse immunoglobulin G-peroxidase conjugate in TNE/10% FBS. After washing as described above, the reaction was developed with O-phenylenediamine (Invitrogen). The reaction was stopped after 30 min with 2 N $H_2SO_4$, and absorbance was read at 490 nm in a Victor$^3$V 1420 multilabel counter (Perkin Elmer) and $EC_{50}$ concentrations were determined using Microsoft Excel and XLfit 4.1 software.

For cytotoxicity evaluation, HPC cells were treated with compounds as described above in the absence of the genotype 2a virus and cellular viability was monitored using the Cell Titer 96 AQueous One Solution Cell Proliferation Assay (Promega). Plates were then read at 490 nm in a Victor$^3$V 1420 multilabel counter (Perkin Elmer) and $CC_{50}$ concentrations were determined using Microsoft Excel and XLfit 4.1 software.

Luciferase Replicon Assay

The HCV luciferase replicon assay measures the ability of a test compound to inhibit HCV replication in cell culture after 3 days of treatment in a human hepatoma cell line (Huh-7) bearing an HCV replicon containing a luciferase-neomycin phosphotransferase fusion gene. The inhibition of HCV replication was measured by quantification of luciferase protein expression. Briefly, Huh-7 cells containing either the HCV genotype 1a H77 strain or genotype 1b Con1 strain subgenomic luciferase replicon (H1a-luc or Zluc, respectively) were grown in DMEM containing glucose, L-glutamine and sodium pyruvate, 10% fetal bovine serum (FBS), 100 IU/mL penicillin, 100 µg/mL streptomycin, 2 mM GlutaMAX, non-essential amino acids and 0.25 (H1a-luc) or 0.5 (Zluc) mg/mL G418. GlutaMAX was obtained from Invitrogen, Corp.; all other media reagents were obtained from Mediatech, Inc. For dose-response testing, the cells were seeded in 96-well plates at $1\times10^4$ (H1a-luc) or $7.5\times10^3$ (Zluc) cells/well in a volume of 50 µL, and incubated at 37° C./5% $CO_2$. Three hours after plating, 50 µL of ten 5-fold serial dilutions of compound were added, and cell cultures were incubated at 37° C./5% $CO_2$ for 72 hours. In all cases, Huh-7 cells lacking the HCV replicon served as negative control. To assess luciferase expression, the media/compound was removed from the plates and ONE-glo Luciferase assay reagent (Promega) was added to each well. The assay plates were shaken for 3 minutes at room temperature and luciferase activity for each well was measured with a 1 sec read time on the Victor$^3$V multilabel counter using a 700 nm cut-off filter (Perkin Elmer). $EC_{50}$ values were calculated from dose response curves from the resulting best-fit equations determined by Microsoft Excel and XLfit 4.1 software.

For cytotoxicity evaluation, H1a-luc or Zluc cells were treated with compounds as described above and cellular viability was monitored using the Cell Titer 96 AQueous One Solution Cell Proliferation Assay (Promega). Plates were then read at 490 nm in a Victor$^3$V 1420 multilabel counter (Perkin Elmer) and $CC_{50}$ concentrations were determined using Microsoft Excel and XLfit 4.1 software.

Luciferase Replicon Transient Transfection Assay

General procedure: The luciferase replicon transient transfection assay measures the ability of a test compound to inhibit the replication of a transiently-transfected HCV luciferase-bearing wild-type or mutant replicon in cured human hepatoma cells (Huh7.5). The inhibition of HCV replication was measured by quantification of luciferase protein expression. This assay has been validated using a panel of genotype 1a and 1b replicons bearing mutations known to be associated with resistance to BMS-790052. Briefly, subconfluent Huh7.5 cells were electroporated with 10 µg of wild-type or mutant luciferase-bearing HCV replicon RNA. The cells were then seeded in 96-well opaque white plates at $3\times10^4$ cells/well in 150 µL/well and incubated for 4 hrs at 37° C./5% $CO_2$. Ten 1:5 serial dilutions of each test compound were made in media (DMEM containing glucose, L-glutamine and sodium pyruvate, 10% fetal bovine serum, 100 IU/mL penicillin, 100 µg/mL streptomycin, 2 mM GlutaMAX, and 1×MEM non-essential amino acids (Mediatech, Inc. and Invitrogen Corp.)) at concentrations that were 4× higher than the final concentrations to be tested and 50 µL/well was added to the transfected cells. Untreated, mock-transfected cells served as a negative control of luciferase expression. The plates were incubated at 37° C./5% $CO_2$ for 4 days whereupon the media was removed and 50 µL of ONE-glo luciferase substrate (Promega) was added to each well. The plates were agitated on a rotating platform at room temperature for 3 min and read in a Victor$^3$V microplate reader (Perkin-Elmer) using a 700 nm cut-off filter with a 1 sec read time. $EC_{50}$ values were calculated from dose response curves from the resulting best-fit equations determined by Microsoft Excel and XLfit 4.1 software.

To determine the replication capacity of each mutant relative to the wild-type parental replicon, transfected cells were plated on two plates and were not treated with compound. Luciferase activity was measured at time points of 4 hrs and 4 days after plating for each replicon. Replication capacity was calculated by dividing the day 4 CPS by the 4 hour CPS for each replicon and determining the percentage present for each mutant replicon relative to wild-type replicon values. The NS3, NS4B, and NS5B mutants were prepared and tested according to the methods described herein.

The compounds disclosed herein (ID corresponds to compound number) have $IC_{50}$ as follows:

| ID | 1a $IC_{50}$ (nM) | 1aY93H $IC_{50}$ (nM) | 1b $IC_{50}$ (nM) | 2b $IC_{50}$ (nM) | 3a $IC_{50}$ (nM) |
|---|---|---|---|---|---|
| 1 | 0.0204 | 66.03 | | | |
| 2 | 0.0046 | 10.55 | 0.0036 | 37.11 | 1.383 |
| 3 | 0.0022 | 7.152 | 0.0016 | 1.953 | 0.721 |
| 4 | 0.0057 | 48.76 | | | |
| 5 | 0.0050 | 11.73 | | 0.784 | 1.085 |
| 6 | 0.0027 | 15.01 | | 12.81 | 1.718 |
| 7 | 0.0029 | 17.83 | | 11.02 | |
| 8 | 0.0020 | 4.103 | | 3.333 | 0.581 |
| 9 | 0.0020 | 3.28 | | 4.533 | 1.112 |
| 10 | 0.0122 | 13.05 | | 5.494 | 0.114 |
| 11 | 0.0037 | 0.391 | 0.0044 | 0.016 | 0.038 |
| 12 | 0.0045 | 0.548 | 0.0056 | 0.495 | 0.055 |
| 13 | 0.0023 | 0.682 | 0.0040 | 0.254 | 0.084 |
| 14 | 0.0042 | 0.221 | | | 0.034 |
| 15 | 0.0098 | 0.826 | 0.0036 | 0.292 | 0.218 |
| 16 | 0.0036 | 0.072 | 0.0044 | 0.032 | 0.015 |
| 17 | 0.0034 | 0.046 | 0.0305 | 0.028 | 0.055 |
| 18 | 208.1 | 146.6 | | | |
| 19 | 745 | 1390 | | | |
| 20 | | | | | |
| 21 | 63.13 | 96.21 | | 505 | |
| 22 | 291.1 | 717.3 | | | |
| 23 | 53.48 | 435.7 | | 1000 | |
| 24 | 424.8 | 2465 | | | |
| 25 | 0.167 | 100 | 0.107 | 100 | 1 |
| 26 | 1 | 100 | 1 | 100 | 1 |
| 27 | 1 | 96.56 | 0.5907 | 100 | 1 |
| 28 | 0.0292 | 1.179 | 0.00445 | 89.83 | 1 |
| 29 | 1 | 100 | 1 | 100 | 1 |
| 30 | 0.0416 | 2.03 | | 0.481 | 0.722 |
| 31 | 0.31 | 506 | | 797 | 0.0262 |
| 32 | 0.0841 | 0.18 | | 3.47 | 5.84 |
| 33 | 0.003 | 18.38 | 0.003326 | 14.08 | 1 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula (I):

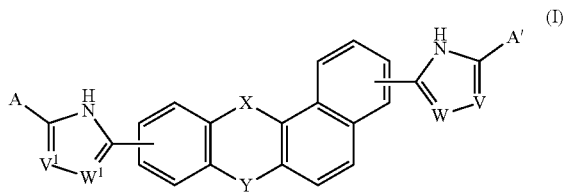

(I)

or a pharmaceutically acceptable salt thereof, wherein:
X is —O—, —C(O)—, —C($R^A R^B$)—, $NR^A$, or $SO_2$;
Y is —O—, —C(O)—, —C($R^A R^B$)—, $NR^A$, or $SO_2$, such that one of X and Y is —O—, and the other of X and Y is other than —O—;

V is CH;
W is N;
$V^1$ is CH;
$W^1$ is N;
$R^A$ is H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, 6 to 10-membered bicyclic heterocycloalkyl, $C_6$-$C_{10}$ aryl, or —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said 6 to 10-membered bicyclic heterocycloalkyl, or said $C_6$-$C_{10}$ aryl group, can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);
$R^B$ is H, halo, —CN, $C_1$-$C_6$ alkyl, $C_1$-$C_6$ haloalkyl, $C_3$-$C_7$ cycloalkyl, 4 to 6-membered monocyclic heterocycloalkyl, 5 or 6-membered monocyclic heteroaryl, 6 to 10-membered bicyclic heterocycloalkyl, $C_6$-$C_{10}$ aryl, or —O—($C_1$-$C_6$ alkyl), wherein said $C_3$-$C_7$ cycloalkyl group, said 4 to 6-membered monocyclic heterocycloalkyl group, said 5 or 6-membered monocyclic heteroaryl group, said 6 to 10-membered bicyclic heterocycloalkyl, or said $C_6$-$C_{10}$ aryl group, can be optionally substituted with up to 3 groups, which can be the same or different, and are selected from halo, —CN, $C_1$-$C_6$ alkyl, $C_1$-$C_6$ haloalkyl, —O—$C_1$-$C_6$ alkyl, —($C_1$-$C_6$ alkylene)-O—$C_1$-$C_6$ alkyl and —O—($C_1$-$C_6$ haloalkyl);
A is:

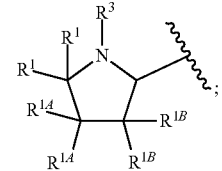

A' is:

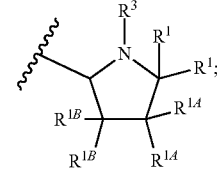

each occurrence of $R^1$ is H;
each occurrence of $R^{1A}$ is independently selected from H, and halo;
each occurrence of $R^{1B}$ is H;
each occurrence of $R^3$ is independently H, —C(O)—C($R^4$)$_2$NHC(O)O—$R^5$, —C(O)O—$R^5$, C(O)NHR$^5$ or —C(O)—C($R^4$)$_2$NR'R$^8$;
each occurrence of $R^4$ is independently selected from H, $C_1$-$C_6$ alkyl, $C_1$-$C_6$ haloalkyl, $C_6$-$C_{10}$ aryl, 4 to 8-membered monocyclic heterocycloalkyl, 6 to 10-membered bicyclic heterocycloalkyl and $C_3$-$C_7$ cycloalkyl, wherein said 4 to 8-membered monocyclic heterocycloalkyl group, said 6 to 10-membered bicyclic heterocycloalkyl group, said C$_6$-C$_{10}$ aryl group and said C$_3$-C$_7$ cycloalkyl group can be optionally substituted with up to 5 groups, each independently selected from halo, —CN, C$_1$-C$_6$ alkyl, C$_1$-C$_6$ haloalkyl, C$_3$-C$_7$ cycloalkyl, —O—C$_1$-C$_6$ alkyl, —N(R$^6$)$_2$ and —O—(C$_1$-C$_6$ haloalkyl), and wherein said C$_3$-C$_7$ cycloalkyl group can be optionally fused to a 4 to 6-membered monocyclic heterocycloalkyl group, and wherein said 4 to 8-membered monocyclic heterocycloalkyl group and said C$_3$-C$_7$ cycloalkyl group can be substituted on a ring carbon atom with a spirocyclic C$_3$-C$_6$ cycloalkyl group; and wherein said C$_3$-C$_7$ cycloalkyl group can be substituted on a ring carbon atom with a spirocyclic 3 to 6-membered monocyclic heterocycloalkyl group, and wherein two R$^4$ groups, that are attached to a common carbon atom, together with the common carbon atom to which they are attached, can join to form a C$_3$-C$_7$ cycloalkyl group;

each occurrence of R$^5$ is independently selected from C$_1$-C$_6$ alkyl, C$_3$-C$_7$ cycloalkyl and C$_6$-C$_{10}$ aryl;

each occurrence of R$^6$ is independently selected from H, C$_1$-C$_6$ alkyl and C$_3$-C$_7$ cycloalkyl;

each occurrence of R$^7$ is independently H, C$_1$-C$_6$ alkyl, C$_1$-C$_6$ haloalkyl, C$_3$-C$_7$ cycloalkyl, or phenyl, or R$^7$ and R$^8$, together with the nitrogen atom to which they are attached, form a 3 to 6-membered monocyclic heterocycloalkyl group; and each occurrence of R$^8$ is independently H, C$_1$-C$_6$ alkyl, C$_1$-C$_6$ haloalkyl, C$_3$-C$_7$ cycloalkyl, or phenyl, or R$^7$ and R$^8$, together with the nitrogen atom to which they are attached, form a 3 to 6-membered monocyclic heterocycloalkyl group.

2. The compound of claim 1, or a pharmaceutically acceptable salt thereof, wherein A and A' are each independently

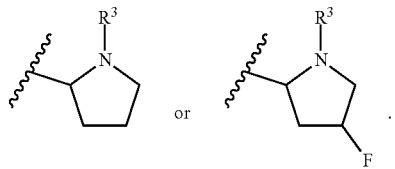

3. The compound of claim 2, or a pharmaceutically acceptable salt thereof, wherein each R$^3$ is independently H, —C(O)CH(CH(CH$_3$)$_2$)(NHC(O)OCH$_3$), —C(O)OC(CH$_3$)$_3$, C(O)NHC(CH$_3$)$_3$,

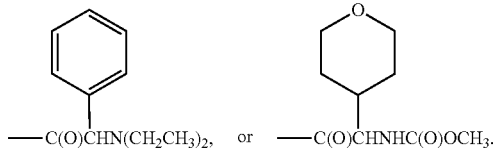

4. The compound of claim 1, or a pharmaceutically acceptable salt thereof, wherein each R$^{14}$ is independently H or fluoro.

5. The compound of claim 1, or a pharmaceutically acceptable salt thereof, wherein R$^A$ and R$^B$ are independently H, halo, or —C$_1$-C$_6$ alkyl.

6. The compound of claim 5, or a pharmaceutically acceptable salt thereof, wherein R$^A$ and R$^B$ are independently H, fluoro, —CH$_3$ or —CH$_2$CH$_3$.

7. The compound of claim 1, or a pharmaceutically acceptable salt thereof, wherein each R$^4$ is independently H, —CH(CH$_3$)$_3$,

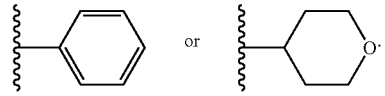

8. The compound of claim 1, or a pharmaceutically acceptable salt thereof, wherein each R$^5$ is independently CH$_3$ or —C(CH$_3$)$_3$.

9. The compound of claim 1, or a pharmaceutically acceptable salt thereof, wherein R$^7$ and R$^8$ are independently H or —C$_1$-C$_6$ alkyl.

10. The compound of claim 1 which is methyl [(1R)-1-({(2R)-2-[5-(9-{2-[(2R)-1-{(2S)-2-[(methoxycarbonyl)amino]-3-methylbutanoyl}pyrrolidin-2-yl]-1H-imidazol-5-yl}-7-oxo-7H-benzo[c]xanthen-3-yl)-1H-imidazol-2-yl]pyrrolidin-1-yl}carbonyl)-2-methylpropyl]carbamate, methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-12-methyl-12H-benzo[a]xanthen-9-yl)-1H-imidazol-2-yl]pyrrolidin-1-yl}carbonyl)-2-methylpropyl] carbamate, methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-12-methyl-12H-benzo[a]xanthen-9-yl)-1H-imidazol-2-yl]pyrrolidin-1-yl}carbonyl)-2-methylpropyl] carbamate, methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-7-methyl-7H-benzo[c]xanthen-9-yl)-1H-imidazol-2-yl]pyrrolidin-1-yl}carbonyl)-2-methylpropyl] carbamate, methyl [(1 S)-1-({(2S)-2-[5-(12-ethyl-3-{2-[(2S)-1-{(2S)-2-[(methoxycarbonyl)amino]3-methylbutanoyl}pyrrolidin-2-yl]-1H-imidazol-5-yl}-12H-benzo[a]xanthen-9-yl)-1H-imidazol-2-yl]pyrrolidin-1-yl}carbonyl)-2-methylpropyl]carbamate, methyl [(1 S)-1-({(2S)-2-[5-(12-ethyl-3-{2-[(2S)-1-{(2S)-2-[(methoxycarbonyl)amino]-3-methylbutanoyl}pyrrolidin-2-yl]-1H-imidazol-5-yl}-12H-benzo[a]xanthen-9-yl)-1H-imidazol-2-yl]pyrrolidin-1-yl}carbonyl)-2-methylpropyl]carbamate, methyl [(1S)-1-({(2S)-2-[5-(3-{2-[(2S)-1-{(2S)-2-[(methoxycarbonyl)amino]-3-methylbutanoyl}pyrrolidin-2-yl]-1H-imidazol-5-yl}-12,12-dimethyl-12H-benzo[a]xanthen-9-yl)-1H-imidazol-2-yl]pyrrolidin-1-yl}carbonyl)-2-methylpropyl]carbamate, methyl [(1R)-1-({(2S)-2-[5-(12,12-diethyl-3-{2-[(2S)-1-{(2S)-2-[(methoxycarbonyl)amino]-3-methylbutanoyl}pyrrolidin-2-yl]-1H-imidazol-5-yl}-12H-benzo[a]xanthen-9-yl)-1H-imidazol-2-yl]pyrrolidin-1-yl}carbonyl)-2-methylpropyl]carbamate, methyl [(1R)-1-({(2S)-2-[5-(12,12-diethyl-9-{2-[(2S)-1-{(2S)-2-[(methoxycarbonyl)amino]-3-methylbutanoyl}pyrrolidin-2-yl]-1H-imidazol-5-yl}-12H-benzo[b]xanthen-3-yl)-1H-imidazol-2-yl]pyrrolidin-1-yl}carbonyl)-2-methylpropyl]carbamate, dimethyl [(12-methyl-12H-benzo[a]xanthene-3,9-diyl)bis{1H-imidazole-5,2-diyl(2S)pyrrolidine-2,1-diyl[(1 S)-2-oxo-1-(tetrahydro-2H-pyran-4-yl)ethane-2,1-diyl]}]biscarbamate, dimethyl [(12-methyl-12H-benzo[a]xanthene-3,9-diyl)bis{1H-imidazole-5,2-diyl(2 S)pyrrolidine-2,1-diyl[(1 S)-2-oxo-1-(tetrahydro-2H-pyran-4-yl)ethane-2,1-diyl]}]biscarbamate, dimethyl [(12,12-dimethyl-12H-benzo[a]xanthene-3,9-diyl)bis{1H-imidazole-5,2-diyl(2 S)pyrrolidine-2,1-diyl[(1 S)-2-oxo-1-(tetrahydro-2H-pyran-4-yl)ethane-2,1-diyl]}]biscarbamate, dimethyl [(12-ethyl-12H-benzo[a]xanthene-3,9-diyl)bis{1H-imidazole-5,2-diyl(2 S)pyrrolidine-2,1-diyl[(1 S)-2-oxo-1-(tetrahydro-2H-pyran-4-yl)ethane-2,1-diyl]}]biscarbamate, dimethyl [(12-ethyl-12H-benzo[a]xanthene-3,9-diyl)bis{1H-imidazole-5,2-diyl(2 S)pyrrolidine-2,1-diyl[(1 S)-2-oxo-1-(tetrahydro-2H-pyran-4-yl)ethane-2,1-diyl]}]biscarbamate, methyl [(1R)-2-[(2R)-2-{5-[12,12-diethyl-9-(2-{(2R)-1-[(2S)-2-[(methoxycarbonyl)amino]-2-(tetrahydro-2H-pyran-4-yl)acetyl]pyrrolidin-2-yl}-1H-imidazol-5-yl)-12H-benzo[a]xanthen-3-yl]-1H-imidazol-2-yl}pyrrolidin-1-yl]-2-oxo-1-(tetrahydro-2H-pyran-4-yl)ethyl]carbamate, 3-{2-[(2S,4R)-4-fluoropyrrolidin-2-yl]-1H-imidazol-5-yl}-9-{2-[(2S,4S)-4-fluoropyrrolidin-2-yl]-1H-imidazol-5-yl}-12H-benzo[a]xanthen-12-one, 6-fluoro-2,9-bis{2-[(2S,4S)-4-fluoropyrrolidin-2-yl]-1H-imidazol-5-yl}-12H-benzo[b]xanthen-12-one, di-tert-butyl (2S,2'S)-2,2'-[(12-oxo-12H-benzo[a]xanthene-3,9-diyl)bis(1H-imidazole-5,2-diyl)]dipyrrolidine-1-carboxylate, (2S,4R,2'S,4'S)-2,2'-[(12-oxo-12H-benzo[a]xanthene-3,9-diyl)bis(1H-imidazole-5,2-diyl)]bis(N-tert-butyl-4-fluoropyrrolidine-1-carboxamide), di-tert-butyl (2S,4R,2'S,4'S)-2,2'-[(12-oxo-12H-benzo[a]xanthene-3,9-diyl)bis(1H-imidazole-5,2-diyl)]bis(4-fluoropyrrolidine-1-carboxylate), methyl [(1S)-1-({(2S)-2-[5-(10-{2-[(2S)-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate, methyl [(1S)-1-({(2S,4R)-4-fluoro-2-[5-(10-{2-[(2S,4R)-4-fluoro-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate, methyl [(1S)-1-({(2S,4R)-4-fluoro-2-[5-(9-{2-[(2S,4R)-4-fluoro-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate, dimethyl [(12-oxo-12H-benzo[a]xanthene-3,9-diyl)bis{1H-imidazole-5,2-diyl(2 S)pyrrolidine-2,1-diyl[(1 S)-2-oxo-1-(tetrahydro-2H-pyran-4-yl)ethane-2,1-diyl]}]biscarbamate, 3,9-bis(2-{(2S,4R)-1-[(2R)-2-(diethylamino)-2-phenylacetyl]-4-fluoropyrrolidin-2-yl}-1H-imidazol-5-yl)-12H-benzo[a]xanthen-12-one, dimethyl [(12-oxo-12H-benzo[a]xanthene-3,9-diyl)bis{1H-imidazole-5,2-diyl[(2S,4R)-4-fluoropyrrolidine-2,1-diyl][(1 S)-2-oxo-1-(tetrahydro-2H-pyran-4-yl)ethane-2,1-diyl]}]biscarbamate, or methyl [(1 S)-1-({(2S)-2-[5-(9-{2-[(2S)-1-{(2S)-2-[(methoxycarbonyl)amino]-3-methylbutanoyl}pyrrolidin-2-yl]-1H-imidazol-5-yl}-12-oxo-12H-benzo[a]xanthen-3-yl)-1H-imidazol-2-yl]pyrrolidin-1-yl}carbonyl)-2-methylpropyl]carbamate, or a pharmaceutically acceptable salt thereof.

11. A pharmaceutical composition comprising the compound of claim 1, or a pharmaceutically acceptable salt thereof, and one or more pharmaceutically acceptable carriers.

12. The pharmaceutical composition of claim 11, further comprising a second antiviral agent.

13. The pharmaceutical composition of claim 12, wherein the second antiviral agent is selected from an interferon, ribavirin, an interleukin, an NS3 protease inhibitor, a cysteine protease inhibitor, a phenathrenequinone, a thiazolidine, a benzanilide, a helicase inhibitor, a polymerase inhibitor, a nucleotide analogue, a liotoxin, acerulenin, an antisense phosphorothioate oligodeoxynucleotide, an inhibitor of IRES-dependent translation, or a ribozyme.

\* \* \* \* \*